(12) United States Patent
Veliss et al.

(10) Patent No.: US 9,901,699 B2
(45) Date of Patent: Feb. 27, 2018

(54) PAD FOR A MASK

(75) Inventors: Lee James Veliss, West Ryde (AU); Scott Alexander Howard, Harbord (AU); Luke Maguire, Stanmore (AU); Donald Darkin, Dural (AU); Philip Rodney Kwok, Chatswood (AU); Alicia Kristianne Wells, Narrabeen (AU); Adam Barlow, Lilyfield (AU)

(73) Assignee: RESMED LIMITED, Bella Vista (AU)

( * ) Notice: Subject to any disclaimer, the term of this patent is extended or adjusted under 35 U.S.C. 154(b) by 656 days.

(21) Appl. No.: 12/801,377

(22) Filed: Jun. 4, 2010

(65) Prior Publication Data

US 2011/0005524 A1 Jan. 13, 2011

Related U.S. Application Data

(63) Continuation-in-part of application No. 12/478,537, filed on Jun. 4, 2009, now Pat. No. 8,291,906.
(Continued)

(30) Foreign Application Priority Data

Jul. 24, 2009 (AU) ................................ 2009903495

(51) Int. Cl.
*A61M 16/06* (2006.01)
(52) U.S. Cl.
CPC ........ *A61M 16/0666* (2013.01); *A61M 16/06* (2013.01); *A61M 16/0655* (2014.02); *A61M 16/0683* (2013.01); *A61M 16/0688* (2014.02)

(58) Field of Classification Search
CPC .............. A61M 16/06; A61M 16/0683; A61M 2016/0616; A61M 2016/0633;
(Continued)

(56) References Cited

U.S. PATENT DOCUMENTS

| 3,357,426 A | 12/1967 | Cohen |
| 3,594,813 A | 7/1971 | Sanderson |

(Continued)

FOREIGN PATENT DOCUMENTS

| DE | 197 03 526 A1 | 8/1998 |
| EP | 0 466 960 A1 | 1/1992 |

(Continued)

OTHER PUBLICATIONS

Pad-A-Cheek website, available as of May 31, 2010.*
(Continued)

*Primary Examiner* — Kathryn E Ditmer
(74) *Attorney, Agent, or Firm* — Nixon & Vanderhye, P.C.

(57) ABSTRACT

A cushion pad for a mask worn by a patient, comprising a first side to contact skin of the patient, and a second side, opposite the first side, to contact or face the mask. The pad has a main body portion having a central portion shaped to cover a portion of the patient's nose extending from above the nose tip to the nasal bridge region without obstructing the patient's line of sight, and lateral side portions to extend downward and terminate along the sides of the nose or on the patient's cheeks. The main body is made of a breathable material, e.g., foam. The pad may include adhesive and/or an attached portion, e.g., a ring, to couple the pad to the patient and/or portion of the mask.

42 Claims, 23 Drawing Sheets

Related U.S. Application Data

(60) Provisional application No. 61/058,659, filed on Jun. 4, 2008, provisional application No. 61/080,847, filed on Jul. 15, 2008.

(58) Field of Classification Search
CPC .......... A61M 2016/0638; A61M 16/08; A61M 16/0633; A61M 16/0655; A61M 16/0666; A61M 16/0688; A62B 18/025; A41G 7/00; A41G 7/02; A41D 13/11; A41D 13/1153; A42B 1/046; A42B 3/20; A63B 1/10; A61F 9/02; A61F 9/025; A61F 9/029
USPC ............ 128/206.25, 206.24, 202.18, 206.27, 128/207.11, 205.25; 2/9, 206
See application file for complete search history.

(56) References Cited

U.S. PATENT DOCUMENTS

| | | | |
|---|---|---|---|
| 3,682,171 A | 8/1972 | Dali et al. | |
| 3,972,321 A | 8/1976 | Proctor | |
| 4,006,744 A | 2/1977 | Steer | |
| 4,142,527 A | 3/1979 | Garcia | |
| 4,153,051 A | 5/1979 | Shippert | |
| 4,274,402 A | 6/1981 | Shippert | |
| 4,454,881 A * | 6/1984 | Huber ................ | A41D 13/1146 128/206.15 |
| 4,548,200 A | 10/1985 | Wapner | |
| 4,711,636 A | 12/1987 | Bierman | |
| 4,767,411 A | 8/1988 | Edmunds | |
| 4,790,829 A | 12/1988 | Bowden et al. | |
| 4,802,857 A | 2/1989 | Laughlin | |
| 4,838,878 A | 6/1989 | Kalt et al. | |
| 4,919,654 A | 4/1990 | Kalt | |
| 4,966,590 A | 10/1990 | Kalt | |
| 4,969,880 A | 11/1990 | Zamierowski | |
| 4,976,698 A | 12/1990 | Stokley | |
| 5,117,818 A | 6/1992 | Palfy | |
| 5,243,971 A | 9/1993 | Sullivan et al. | |
| 5,261,893 A | 11/1993 | Zamierowski | |
| 5,263,939 A | 11/1993 | Wortrich | |
| 5,304,146 A | 4/1994 | Johnson et al. | |
| 5,364,367 A | 11/1994 | Banks et al. | |
| 5,438,710 A | 8/1995 | McDonald et al. | |
| 5,513,635 A | 5/1996 | Bedi | |
| 5,537,687 A * | 7/1996 | Garza .................... | 2/9 |
| 5,682,881 A | 11/1997 | Winthrop et al. | |
| 5,707,342 A | 1/1998 | Tanaka | |
| 5,735,272 A | 4/1998 | Dillon et al. | |
| 5,752,511 A | 5/1998 | Simmons et al. | |
| 5,807,341 A | 9/1998 | Heim | |
| 5,842,469 A | 12/1998 | Rapp et al. | |
| 5,918,598 A * | 7/1999 | Belfer et al. ............ | 128/206.25 |
| 6,026,811 A | 2/2000 | Settle | |
| 6,095,996 A | 8/2000 | Steer et al. | |
| 6,119,694 A | 9/2000 | Correa et al. | |
| 6,211,263 B1 | 4/2001 | Cinelli et al. | |
| 6,231,548 B1 | 5/2001 | Bassett | |
| 6,258,066 B1 | 7/2001 | Urich | |
| 6,328,038 B1 * | 12/2001 | Kessler et al. ........... | 128/207.18 |
| 6,338,340 B1 | 1/2002 | Finch et al. | |
| 6,341,606 B1 * | 1/2002 | Bordewick et al. ..... | 128/206.25 |
| 6,358,279 B1 | 3/2002 | Tahi et al. | |
| 6,419,660 B1 | 7/2002 | Russo | |
| 6,419,687 B1 * | 7/2002 | Berke ...................... | 606/204.45 |
| 6,423,036 B1 | 7/2002 | Van Huizen | |
| 6,434,796 B1 | 8/2002 | Speirs | |
| 6,448,303 B1 | 9/2002 | Paul | |
| 6,482,178 B1 | 11/2002 | Andrews et al. | |
| 6,532,961 B1 * | 3/2003 | Kwok .................. | A61M 16/06 128/205.25 |
| 6,533,410 B1 | 3/2003 | Shefler et al. | |
| 6,561,192 B2 | 5/2003 | Palmer | |
| 6,579,267 B2 | 6/2003 | Lynch et al. | |
| 6,607,516 B2 | 8/2003 | Cinelli et al. | |
| 6,663,600 B2 | 12/2003 | Bierman et al. | |
| 6,669,712 B1 | 12/2003 | Cardoso | |
| 6,710,099 B2 | 3/2004 | Cinelli et al. | |
| 6,886,564 B2 * | 5/2005 | Sullivan et al. ......... | 128/206.24 |
| 6,972,003 B2 | 12/2005 | Bierman et al. | |
| 7,018,362 B2 | 3/2006 | Bierman et al. | |
| 7,076,282 B2 | 7/2006 | Munro et al. | |
| 7,146,976 B2 | 12/2006 | McKown | |
| 7,152,601 B2 | 12/2006 | Barakat et al. | |
| 7,207,328 B1 | 4/2007 | Altemus | |
| D552,733 S | 10/2007 | Criscuolo et al. | |
| 7,472,703 B2 * | 1/2009 | Hernandez ............ | A61M 16/06 128/206.21 |
| 8,113,202 B2 * | 2/2012 | Ho ........................ | A61M 16/06 128/206.21 |
| 8,365,733 B2 * | 2/2013 | Rutan ...................... | 128/206.24 |
| 2002/0066452 A1 | 6/2002 | Kessler et al. | |
| 2002/0143296 A1 | 10/2002 | Russo | |
| 2002/0157673 A1 | 10/2002 | Kessler et al. | |
| 2002/0185134 A1 | 12/2002 | Bishop | |
| 2003/0023182 A1 | 1/2003 | Mault et al. | |
| 2004/0106891 A1 | 6/2004 | Langan et al. | |
| 2004/0111104 A1 | 6/2004 | Schein et al. | |
| 2004/0127856 A1 | 7/2004 | Johnson | |
| 2004/0216746 A1 | 11/2004 | Jones, Jr. et al. | |
| 2004/0226564 A1 | 11/2004 | Persson | |
| 2005/0051171 A1 | 3/2005 | Booth | |
| 2005/0101933 A1 | 5/2005 | Marrs et al. | |
| 2006/0095008 A1 | 5/2006 | Lampropoulos et al. | |
| 2006/0095009 A1 | 5/2006 | Lampropoulos et al. | |
| 2007/0163594 A1 | 7/2007 | Ho et al. | |
| 2007/0282272 A1 | 12/2007 | Bannon et al. | |
| 2008/0004573 A1 | 1/2008 | Kaufmann et al. | |
| 2008/0065022 A1 | 3/2008 | Kyvik et al. | |
| 2008/0110469 A1 | 5/2008 | Weinberg | |
| 2008/0200880 A1 | 8/2008 | Kyvik et al. | |
| 2008/0302365 A1 * | 12/2008 | Cohen .................. | A61M 16/06 128/206.12 |
| 2009/0044908 A1 * | 2/2009 | Behrens et al. ............. | 156/329 |
| 2009/0107507 A1 * | 4/2009 | Moore .............. | A61M 16/0683 128/206.24 |
| 2009/0139525 A1 | 6/2009 | Schirm | |
| 2009/0223522 A1 * | 9/2009 | Hernandez ........ | A61M 16/0605 128/206.26 |
| 2009/0229610 A1 * | 9/2009 | Oates et al. .............. | 128/204.21 |
| 2009/0293880 A1 * | 12/2009 | Rutan ...................... | 128/206.21 |
| 2010/0000534 A1 | 1/2010 | Kooij et al. | |
| 2010/0018535 A1 | 1/2010 | Chimenti et al. | |
| 2010/0031958 A1 * | 2/2010 | Stewart .................. | A62B 18/08 128/203.29 |
| 2011/0209701 A1 * | 9/2011 | Derringer et al. ........ | 128/202.17 |

FOREIGN PATENT DOCUMENTS

| | | |
|---|---|---|
| EP | 0 776 679 A1 | 6/1997 |
| WO | WO 98/23305 A1 | 6/1998 |
| WO | WO 99/16327 A1 | 4/1999 |
| WO | WO 99/25410 A1 | 5/1999 |
| WO | WO 00/50121 A1 | 8/2000 |
| WO | WO 02/38221 A1 | 5/2002 |
| WO | WO 2007/143772 A2 | 12/2007 |
| WO | WO 2009/146313 A1 | 12/2009 |
| WO | WO 2010/011575 A1 | 1/2010 |

OTHER PUBLICATIONS

Pad-A-Cheek website, http://www.padacheek.com/PAC_Masklin-ers.html, available as of May 31, 2010.*
RedMed, Ultra Mirage Full Face Mask User Guide, copyright 2005.*
Adam J. Singer MD et al., "The Cyanoacrylate Topical Skin Adhesives," American Journal of Emergency Medicine, vol. 26, 2008, pp. 490-496.
Subbu Venkatraman et al., "Review Skin Adhesives and Skin Adhesion 1. Transdermal Drug Delivery Systems," Biomaterials, vol. 19, 1998, pp. 1119-1136.

(56) References Cited

OTHER PUBLICATIONS

Hans Rudolph, Inc., "A New Nasal CPAP/Bilevel Mask", 1 page.
GaleMed Corporation Components Supply Brochure, 30 pages.
Chimenti et al., U.S. Appl. No. 61/083,480, filed Jul. 24, 2008.
Kooij, et al., U.S. Appl. No. 61/080,847, filed Jul. 15, 2008.
Joel W. Beam, "Tissue Adhesives for Simple Traumatic Lacerations," Journal of Athletic Training, 2008, vol. 43, No. 2, pp. 222-224.
Extended European Search Report dated Sep. 3, 2009 in corresponding EP Application No. 09161984.1.
Doherty et al., U.S. Appl. No. 12/734,498, filed May 5, 2010.
Rummery et al., U.S. Appl. No. 12/763,467, filed Apr. 20, 2010.
Chinese Office Action for Application No. 201010198269.7 w/ English translation dated Jan. 27, 2014, 16 pages.
GaleMed Mask Photo 1, 1 page.
GaleMed Mask Photo 2, 1 page.
GaleMed Pad Photo 1, 1 page.
GaleMed Pad Photo 2, 1 page.
Chinese Office Action for Application No. 201010198269.7 w/ English translation dated Oct. 8, 2014, 14 pages.
Notification of the Third Office Action issued in Application No. 201010198269.7 w/ English translation dated Apr. 22, 2015, 10 pages.

* cited by examiner

PAD FOR A MASK

CROSS REFERENCE TO PRIORITY APPLICATIONS

This application claims the benefit of Australian Application No. AU 2009903495, filed Jul. 24, 2009 and is a continuation-in-part of U.S. application Ser. No. 12/478,537, filed Jun. 4, 2009, now U.S. Pat. No. 8,291,906, which in turn claims the benefit of U.S. Provisional Application No. 61/058,659, filed Jun. 4, 2008 and No. 61/080,847, filed Jul. 15, 2008, each incorporated herein by reference in its entirety.

FIELD OF THE INVENTION

The present invention relates to a pad for a respiratory mask for the delivery of respiratory therapy to a patient. Various respiratory conditions include Sleep Disordered Breathing (SDB) and particularly Obstructive Sleep Apnea (OSA). Respiratory therapies used to treat these conditions include Continuous Positive Airway Pressure (CPAP), Non-Invasive Positive Pressure Ventilation (NIPPY), and Variable Positive Airway Pressure (VPAP).

BACKGROUND OF THE INVENTION

Typically, respiratory therapy is delivered in the form of a respiratory mask or mask system positioned between a patient and apparatus providing a supply of pressurized air or breathing gas. Mask systems in the field of the invention differ from mask systems used in other applications such as aviation and safety in particular because of their emphasis on comfort. This high level of comfort is desired because patients must sleep wearing the masks for hours, possibly every night for the rest of their lives. In addition, therapy, compliance can be improved if the patient's bed partner is not adversely affected by the patient's therapy and wearing of the mask generally.

Mask systems typically, although not always, comprise (i) a rigid or semi-rigid portion often referred to as a shell or frame, (ii) a soft, patient contacting portion often referred to as a cushion, and (iii) some form of headgear to hold the frame and cushion in position. If the mask system does include multiple components, at least some assembly and adjustment may be required, which can be difficult for patients who may suffer from lack of dexterity, etc. Further, mask systems often include a mechanism for connecting an air delivery conduit. The air delivery conduit may preferably be connected to a blower or flow generator.

A range of mask systems are known including nasal masks, nose & mouth masks, full face masks and nasal prongs, pillows, nozzles & cannulae. Masks typically cover more of the face than nasal prongs, pillows, nozzles and cannulae.

Some respiratory masks cause discomfort or are difficult to seal on some patients. Comfort and seal may be particularly troublesome in the nasal bridge region. Other portions of the mask system including but not limited to the forehead support and headgear clips may cause discomfort or cause skin breakdown (e.g. ulceration, skin marking, irritation, redness, etc).

SUMMARY OF THE INVENTION

One aspect of the present technology relates to a pad for a mask system.

One form of a pad in accordance with the present technology comprises a pad for a mask system with an adhesive. In another form, no adhesive is used.

In accordance with one aspect of the present technology, a mask system including a cushion is provided. A pad may be removably held in fixed spacial relation with respect to the cushion. In one form the pad may be tethered to the mask system. In one form the pad may be secured at a particular location on the mask so that it does not fall off when the mask is removed from the face. In one form the pad comprises a tether so that the pad may be selectively held at different regions of the cushion to resolve a seal problem at the different regions. In one form the mask system further includes a mechanical fastener to hold a pad. In one form a pad may be tethered to the mask system without requiring the pad to be held in a fixed location with respect to the cushion. In one form in accordance with the present technology, a pad further comprising a tether is provided.

One form of pad in accordance with the present technology relates to a pad for use with a forehead support. In one form a pad comprises a portion for use with a forehead support and a portion for use with a nasal cushion.

Another aspect of the present invention relates to a pad for a mask system with an attachment portion, e.g., the pad is shaped to cover a designated portion of the patient's face, e.g., the forehead, the nasal bridge region, the cheek region and/or the upper lip or lower lip/chin region, and the attachment portion may be releasably connected to the mask system, e.g., a forehead support (dial, joining member, etc.), frame, headgear, and/or headgear clip, etc.

Another aspect of the present invention relates to a cushion pad for a mask worn by a patient, comprising a first side to contact skin of the patient, a second side, opposite the first side, to contact the mask, the pad having a main body portion having a central portion shaped to cover the nasal bridge region of the patient, the main body portion having an attachment portion to attach the cushion pad to the mask.

Another aspect of the present invention relates to a cushion pad for a mask worn by a patient, comprising a first side to contact skin of the patient, and a second side, opposite the first side, to contact or face the mask, the pad having a main body portion having a central portion shaped to cover a portion of the patient's nose extending from above the nose tip to the nasal bridge region without obstructing the patient's line of sight, and lateral side portions to extend downward and terminate along the sides of the nose or on the patient's cheeks, the main body being made of a breathable material.

Another aspect of the present invention relates to a cushion pad for a mask worn by a patient, comprising a first side to contact skin of the patient, and a second side, opposite the first side, to contact or face the mask, the pad having a main body portion having a central portion shaped to cover a portion of the patient's nose extending from above the nose tip to the nasal bridge region without obstructing the patient's line of sight, and lateral side portions to extend downward along the sides of the nose, the main body being made of a conformable material.

Another aspect of the invention relates to methods of manufacturing a mask pad, e.g., via thermoforming, molding, machining, stitching, die cutting and/or compression cutting.

BRIEF DESCRIPTION OF THE DRAWINGS

The accompanying drawings facilitate an understanding of various embodiments of the present technology.

FIG. 5 shows a perspective view of a first embodiment of the present invention in use.

DETAILED DESCRIPTION

A mask system typically includes a frame, a cushion and a headgear. The frame may anchor the cushion in position and allow for attachment of a headgear. The frame is typically a rigid or semi rigid component constructed of, for example, polycarbonate. The cushion may seal with the face of the patient in order to provide therapy to the patient. The cushion is typically a flexible element constructed of, for example, silicone. The headgear may stabilize and support the frame and cushion in position on the patient's face when in use. The headgear is typically a flexible or semi rigid element constructed of, for example, fabric.

Some patients may have difficulty attaining a seal when the mask system is in position on the patients face (both dynamic and static) for several reasons, such as unique facial profiles. Some patients may experience discomfort, such as irritation due to prolonged contact with the mask system, particularly the cushion. In addition, if the patient has damaged skin that may contact the mask system, the patient may need a pad to reduce pressure and enhance healing at the damaged skin when the mask system is next used. A pad may also reduce rubbing of the patient's hair and thereby reduce hair loss.

The present technology relates to a pad for use with a respiratory mask that may be shaped to cover the nasal bridge, forehead region, or any other area of a patient. The pad may be positioned between the patient and the mask system. The pads may have an adhesive to adhere the pad to the face of the patient and/or to the mask, e.g., the seal and/or another part thereof. The pads may have an anchoring or attachment portion, e.g., a ring, to interface with the mask system so as to secure the pad in position on the mask system.

Pad with Adhesive Attachment

In a first embodiment of the present invention, a pad may be provided for use with a mask system that may attach to the patient and/or mask system by an adhesive. Pad preferably includes breathable and/or conformable material, such as foam.

In a first preferred embodiment, the pad may be provided for the nasal bridge region of the patient, as shown in FIGS. 1-5. The pad 100 has a main body portion that may be generally longer than it is wide, so as to accommodate various nose shapes e.g. nose width and nose bridge height. Pad 100 includes lateral side portions that extend across and/or downwards. Lateral side portions terminate along the sides of the nose or on the patient's cheeks.

Figure 1:
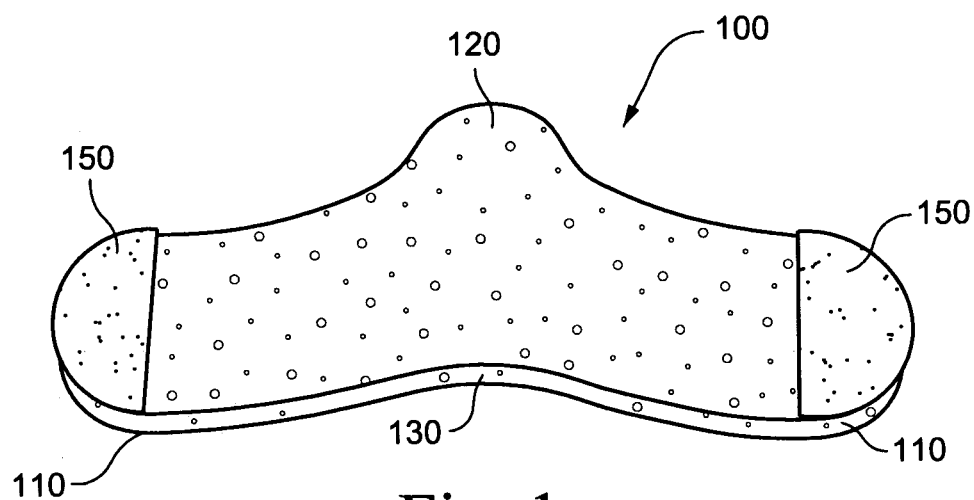
FIG. 1 shows a perspective view of a first embodiment of the present invention.
Figure 2:
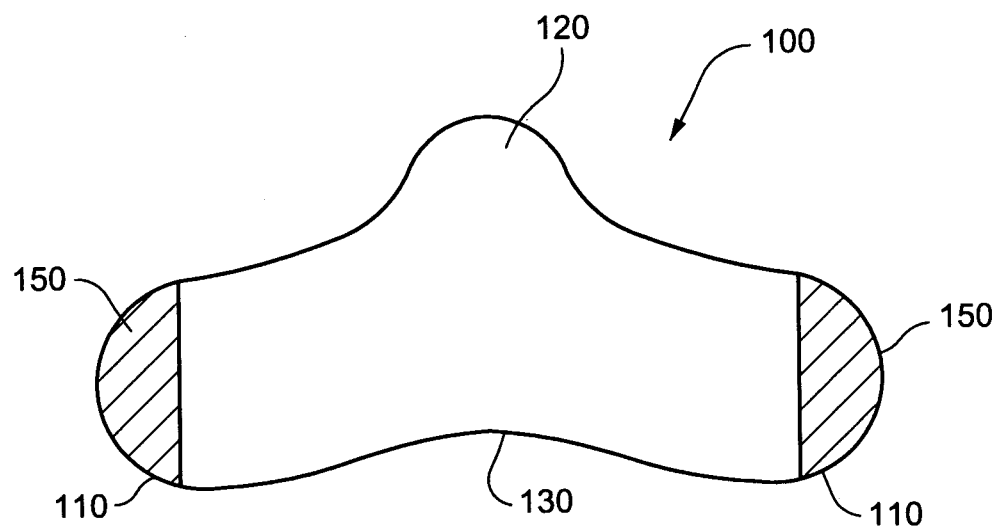
FIG. 2 shows a plan view of a first embodiment of the present invention.

Pad 100 may be generally elliptical, rectangular, trilobular, or any other desired shape (such as that shown in FIGS. 1 and 2).

Pad 100 may include a peak 120 in its central portion so as to fit a wider range of patients (e.g. to conform over a variety of nasal bridge heights). It may also cover more the of nasal bridge region that tends to suffer the most discomfort or damage (since the top of the nose bridge is a small area, it is most susceptible to skin breakdown as the force from the mask system is distributed over a smaller area, also the skin can be thinner in this region when compared to other regions of the face e.g. cheeks).

Peak 120 may be shaped so as to avoid obstructing the patient's line of sight.

Pad 100 may also have a trough 130 so as to avoid the pad extending past the end of the patient's nose when in use. Furthermore, trough 130 and peak 120 may be shaped such that pad 100 can be easily nested when manufactured, thereby increasing yield, reducing waste and reducing part cost.

Pad 100 may be about 5 mm to 60 mm wide. Preferably, pad 100 is about 10 mm to 50 mm. Preferably, pad 100 may be 45 mm wide. Pad 100 may be the same width along the length of the pad. Pad 100 may not have the same width along the length of the pad. Pad may include lateral side portions to extend down and terminate along the sides of the nose, and may extend along the cheeks, and may seal in the nasal crease.

Pad 100 may be about 10 mm to 200 mm long. Preferably, pad 100 may be about 20 mm to 100 mm. Preferably, pad 100 may be about 100 mm long.

Pad 100 may have adhesive 150 at its distal ends 110 (shown in FIGS. 1 and 2), on one entire side of pad 100 or in any region/s of pad 100.

Pad 100 may be about 1 to 15 mm thick. Preferably, pad 100 is about 5 mm thick. Preferably, pad 100 is about 7 mm thick.

The thickness of pad 100 may be constant along the length of the pad. The thickness of pad 100 may vary along its length, e.g. thicker in the middle where the most force from the mask system is applied; or thinner at the distal ends 110 of the pad where the pad no longer contacts the mask system and may cause leaks. Its thickness may vary from the top of the nose to the nasal bridge region, e.g., thicker near nasal bridge region as compared to nose tip.

Pad 100 may be available in multiple sizes to accommodate varying patient facial profiles, e.g., a number of differently shaped pads 100', 100" and 100'" can be packaged within a lot, as shown in FIGS. 5-1, 5-2 and 5-3. Pads may be available in a variety of shapes, see, e.g., FIGS. 5-4 to 5-7, to suit noses of various shapes. For example, FIGS. 5-4 suits flatter noses via a smaller angle, whereas FIG. 5-7 suits sharper noses and has a larger angle, with FIGS. 5-5 and 5-6 being suitable for nose shapes in between. Pad 100 may also be customizable so that patients can vary the size of the pad, e.g. perforations to tear off sections of the pad, or markings to indicate where the patient can cut away portions of the pad to suit their facial profile.

Figure 3:
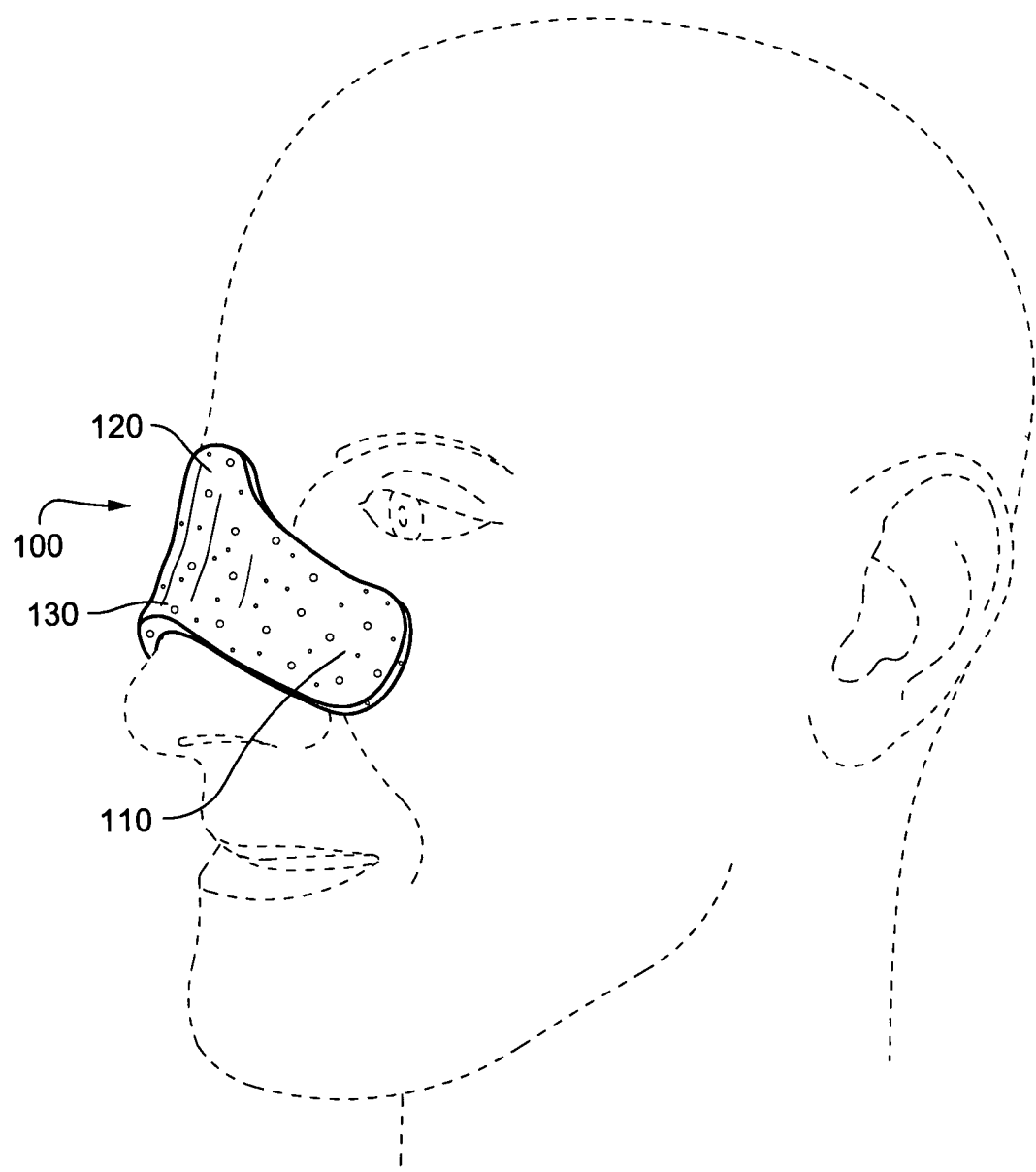
FIG. 3 shows a perspective view of a first embodiment of the present invention in use.
Figure 4:
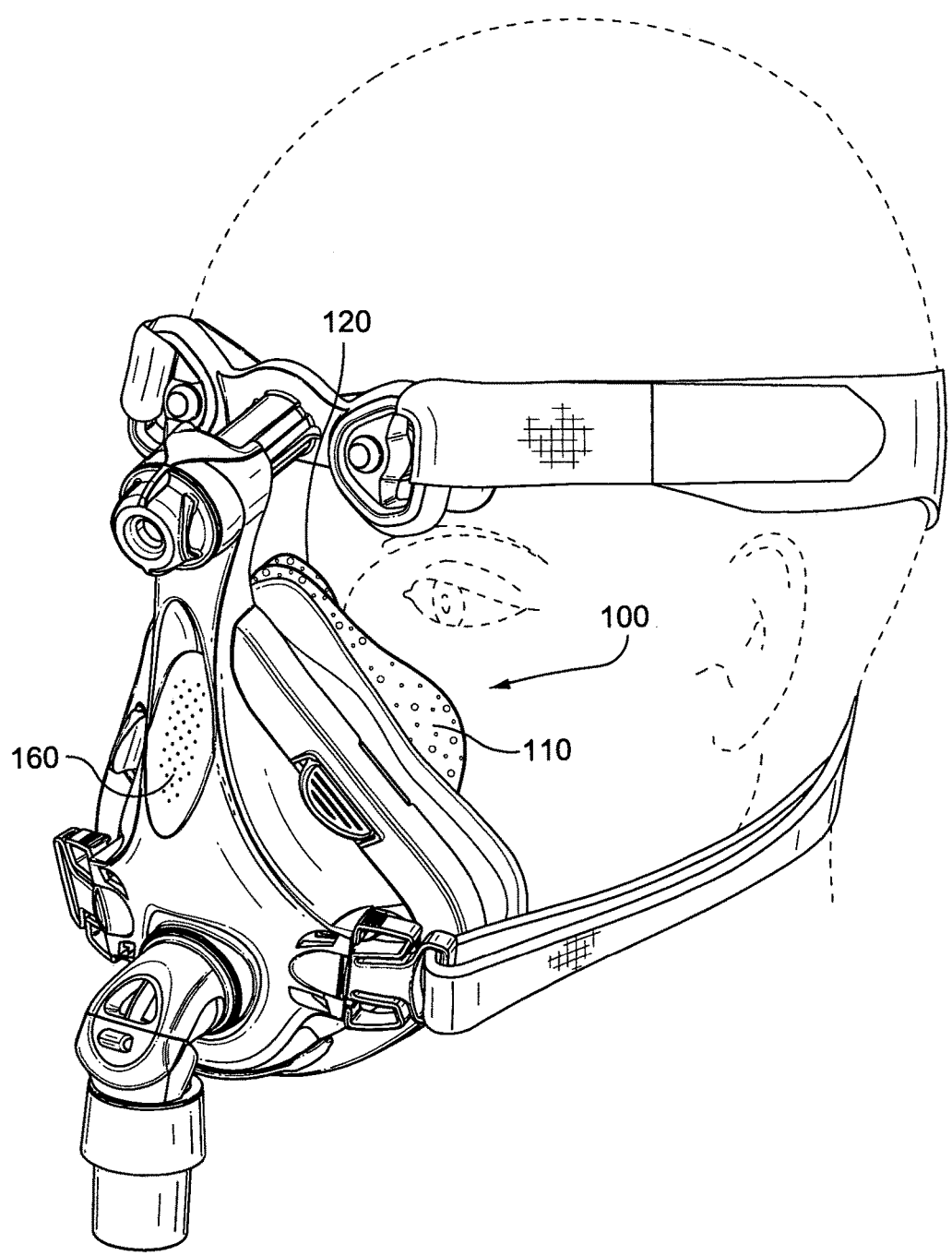
FIG. 4 shows a perspective view of a first embodiment of the present invention in use.
Figure 5:
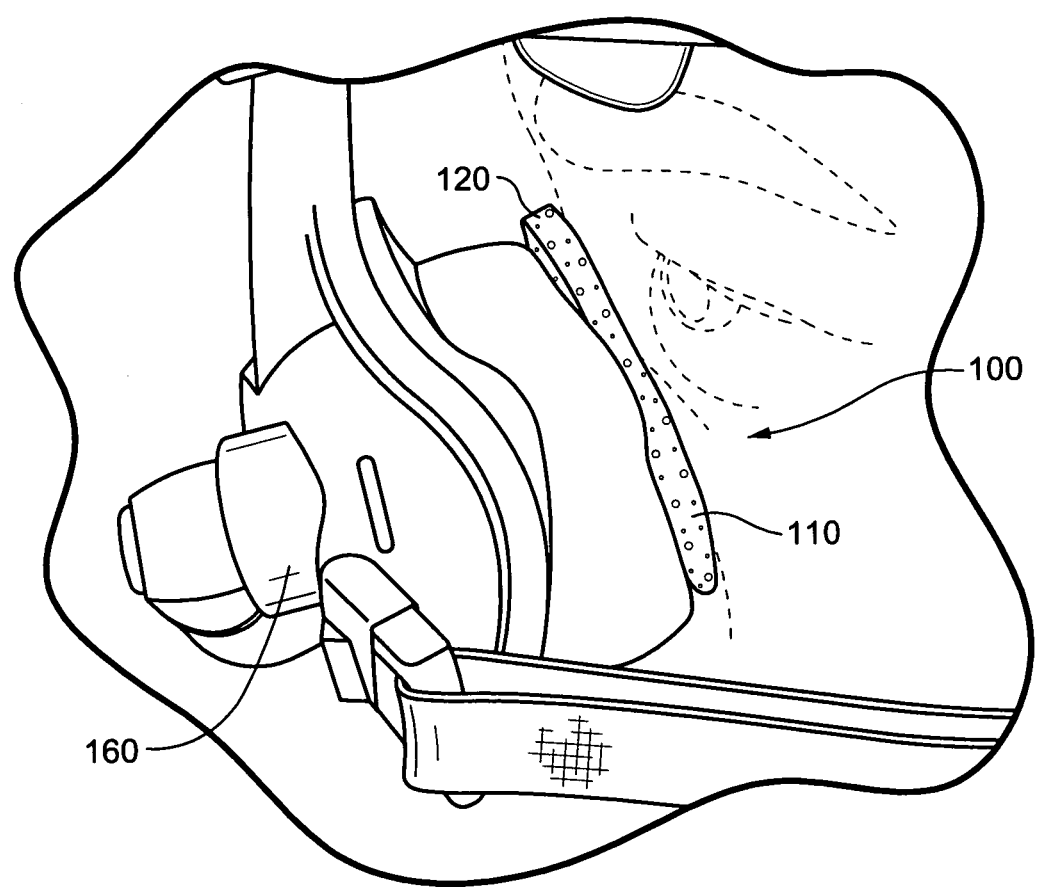
FIGS. 5.1 to 5.7 show alternatives.
Figures 1, 5:
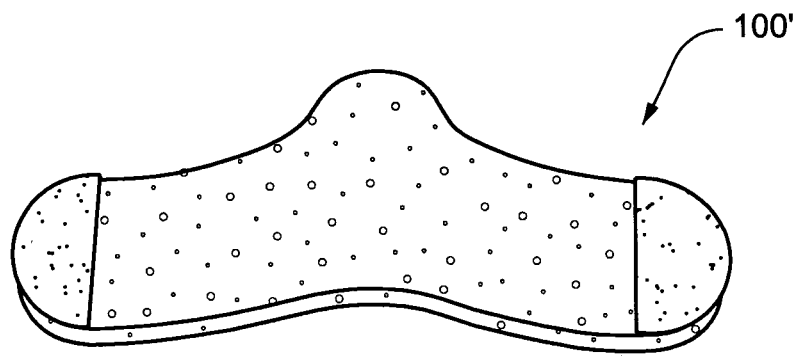
Figures 2, 5:
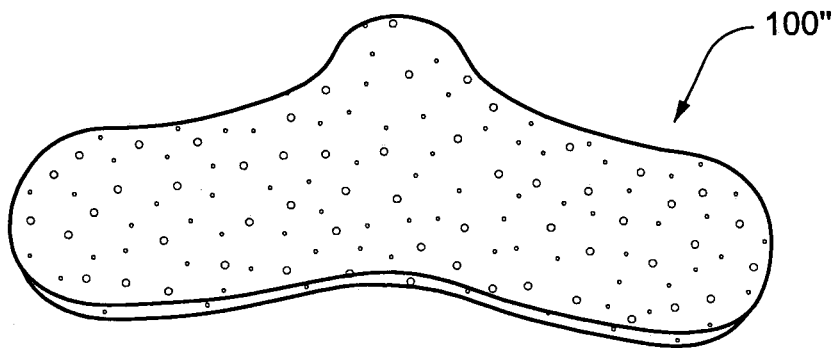
Figures 3, 5:
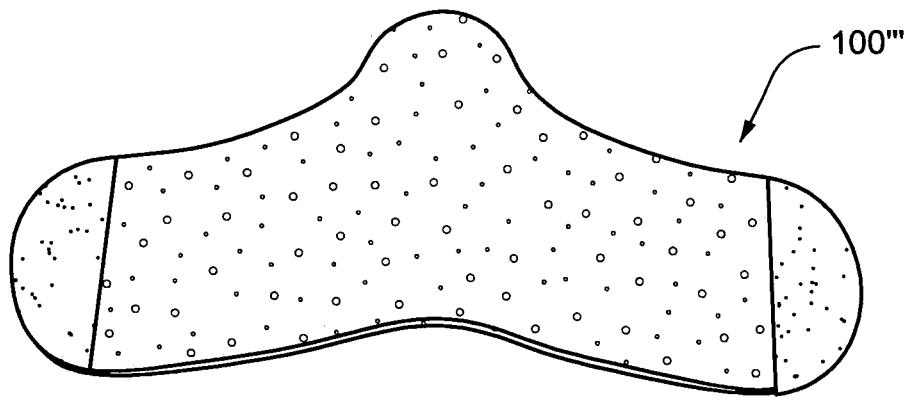
Figures 4, 5:
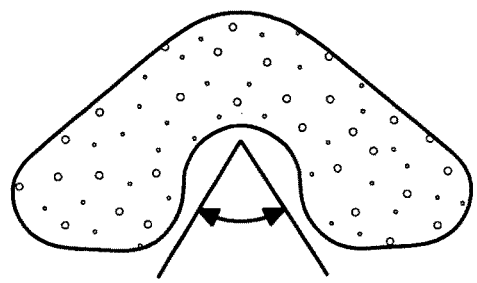
Figure 5:
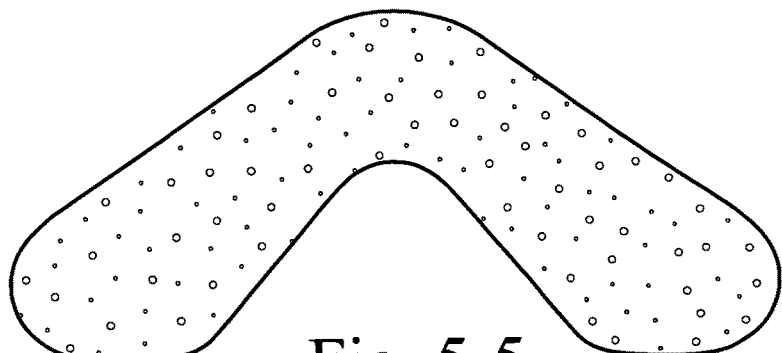
Figures 5, 6:
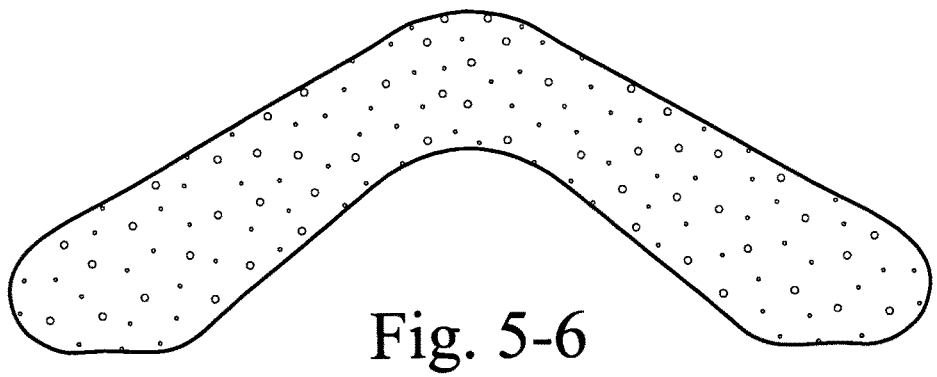
FIG. 6 shows a plan view of a second embodiment of the present invention.
Figures 5, 6, 7:
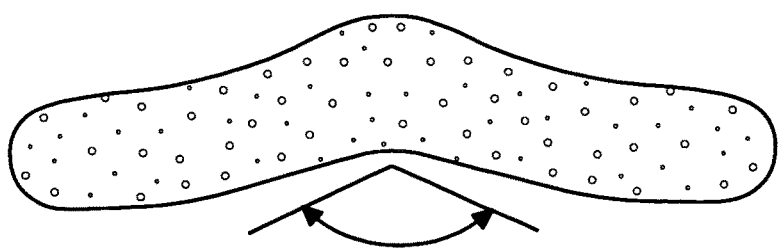
FIG. 7 shows a front view of a second embodiment of the present invention with a mask system.
Figure 6:
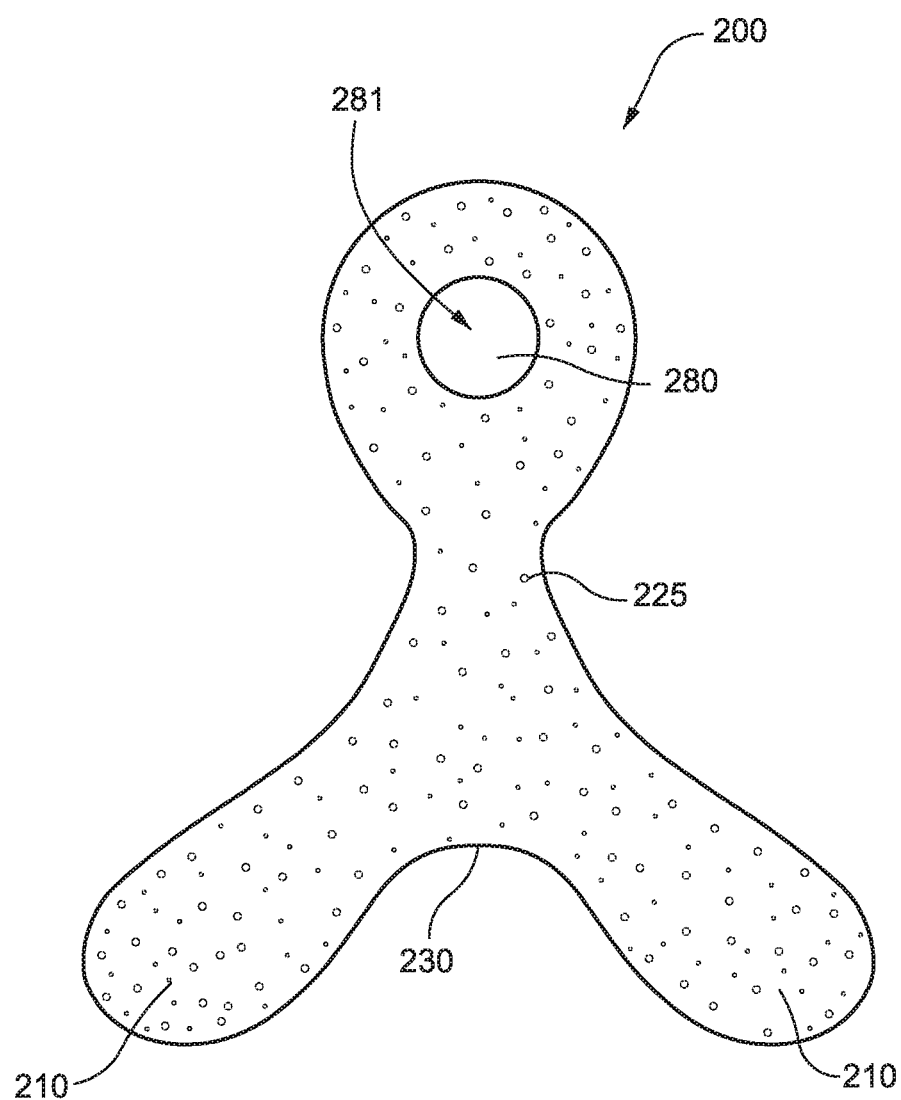
Figure 7:
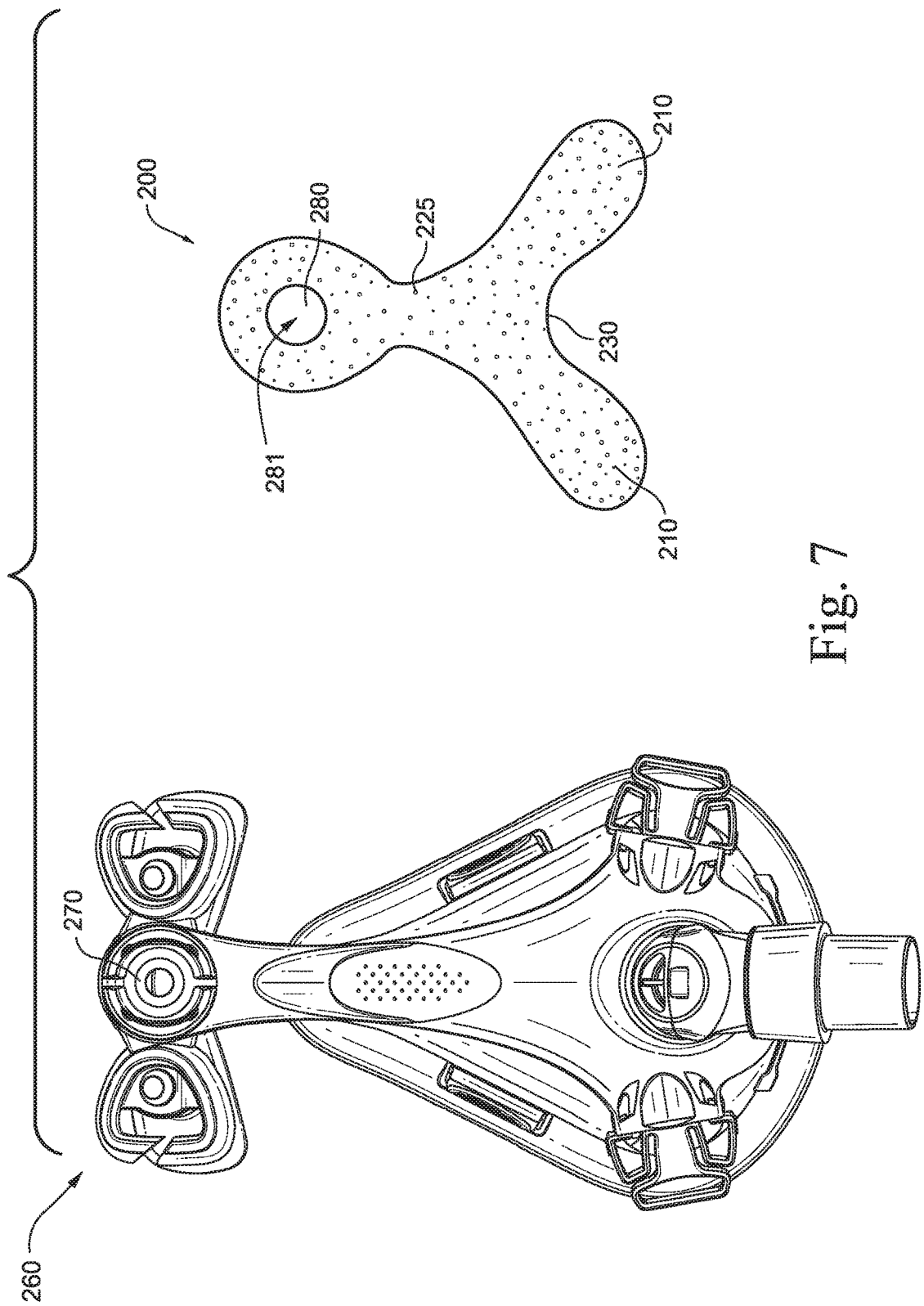
Figure 8:
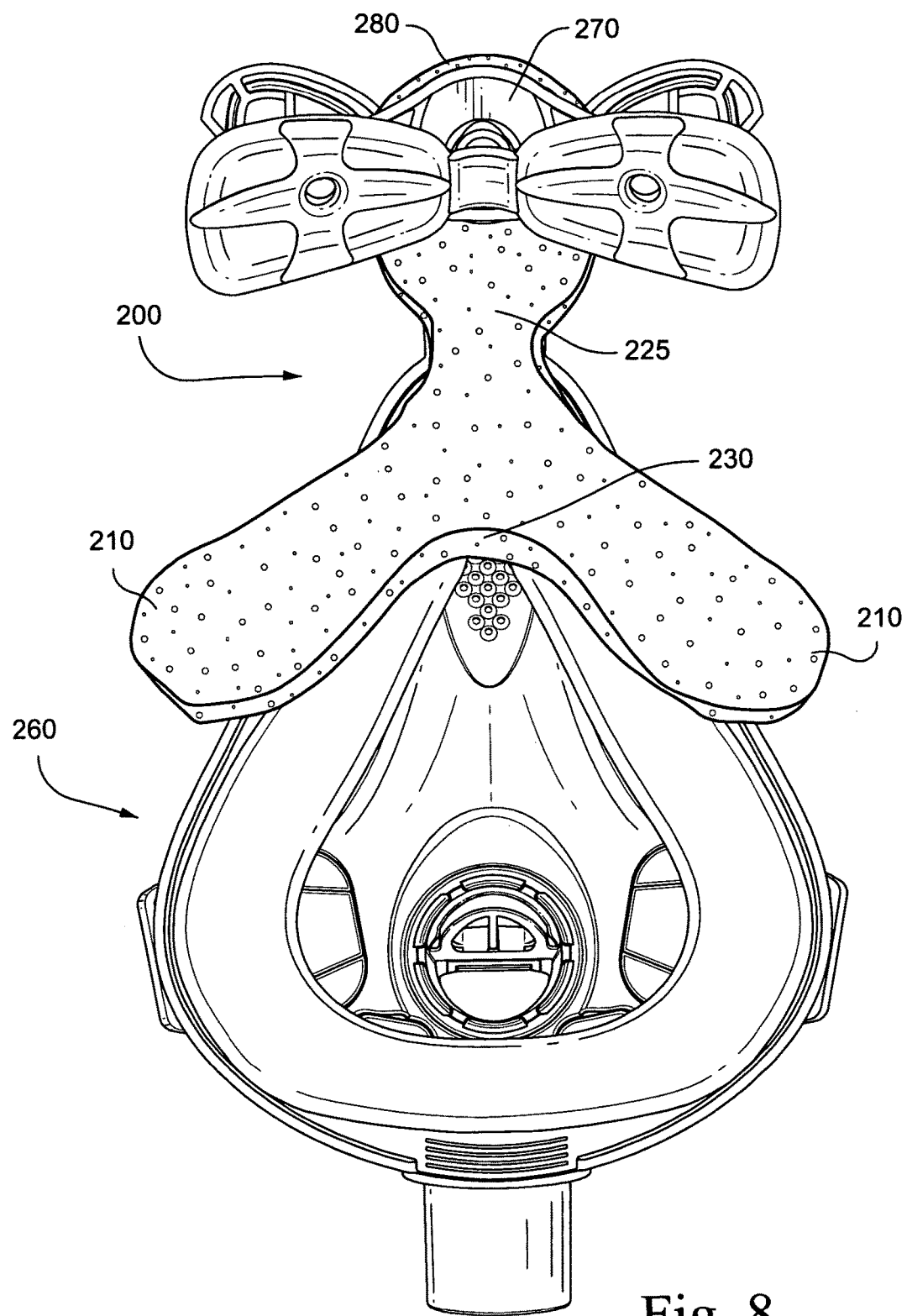
FIG. 8 shows a back view of a second embodiment of the present invention in use.
Figure 9:
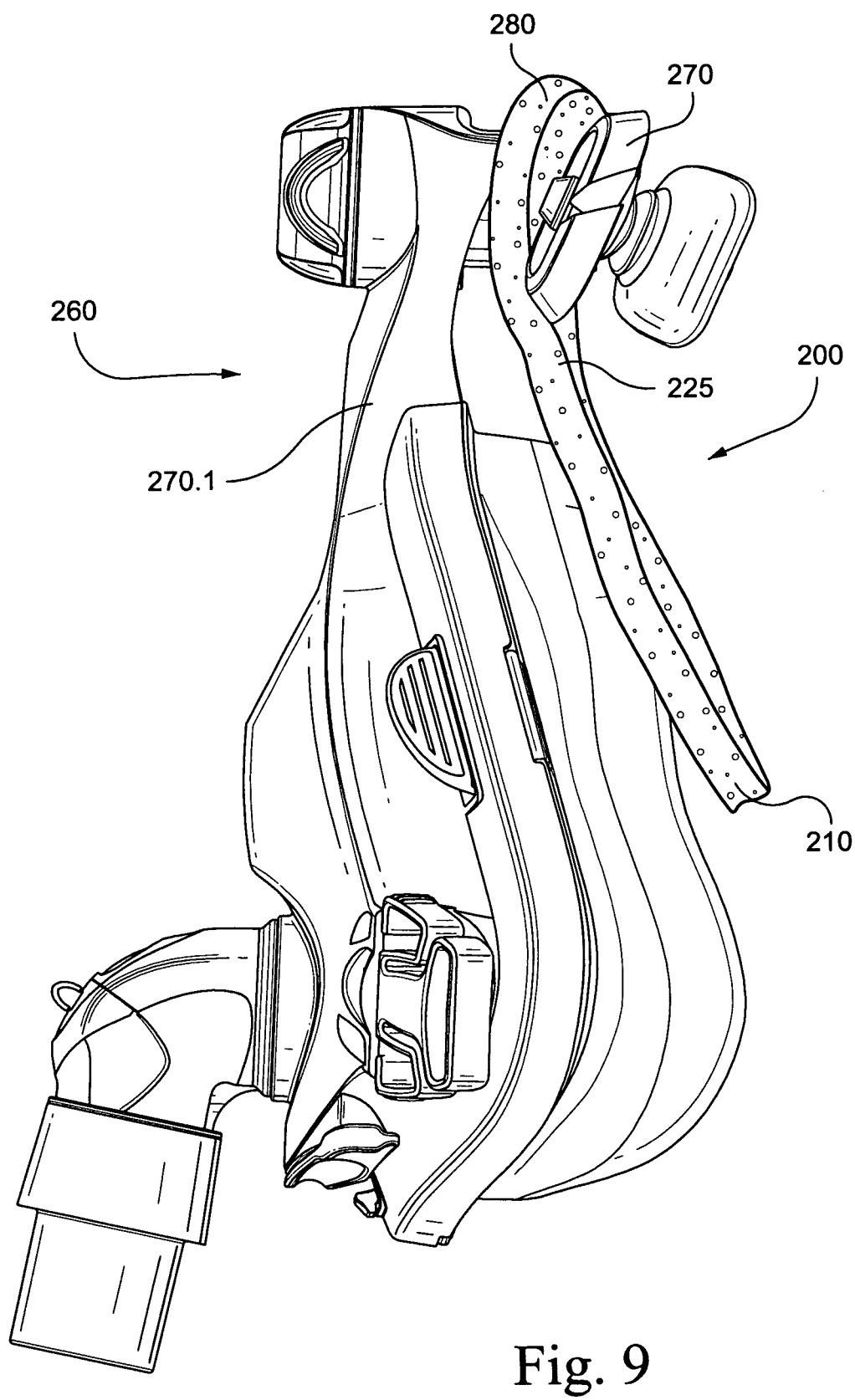
FIG. 9 shows a side view of a second embodiment of the present invention in use.
Figure 10:
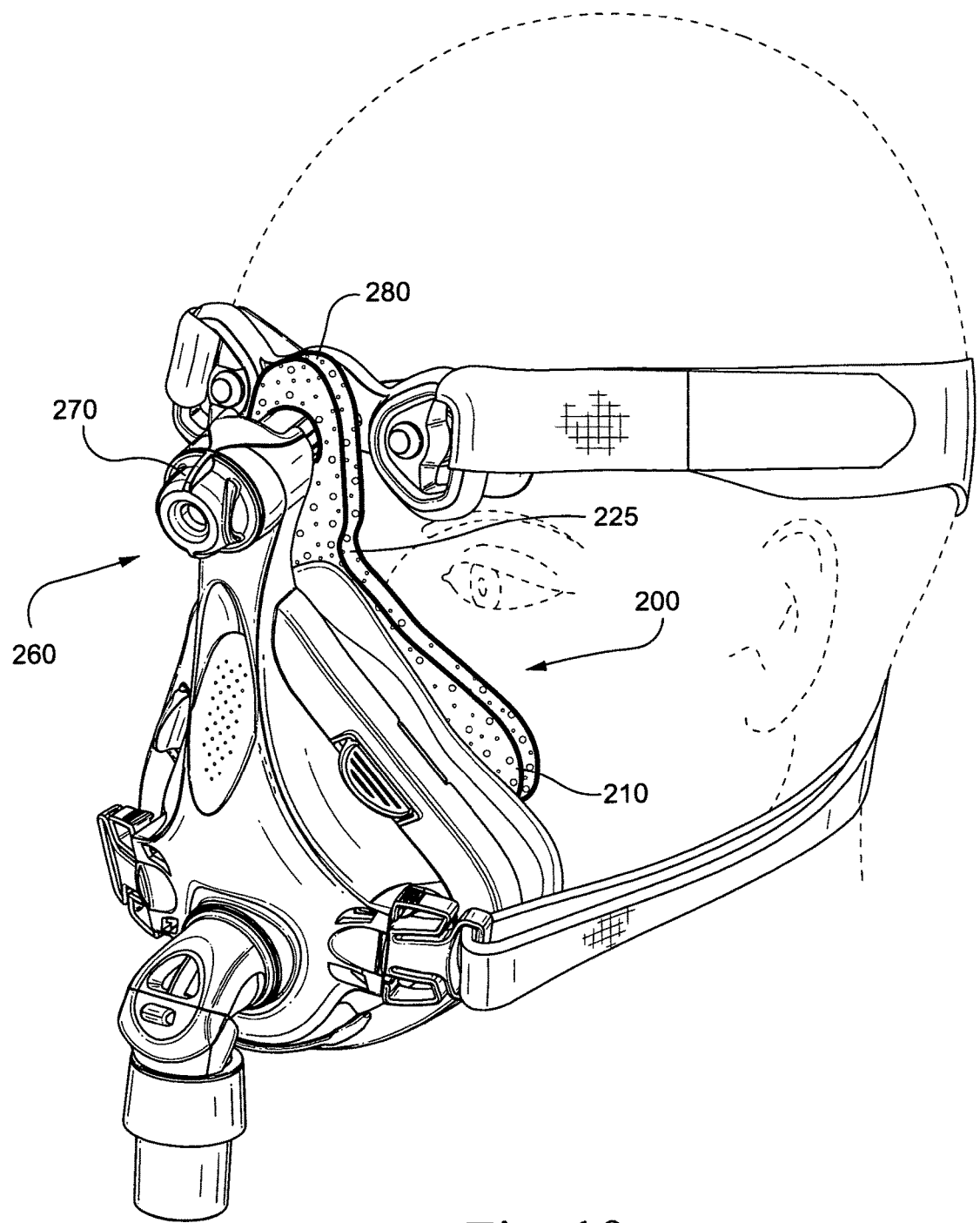
FIG. 10 shows a perspective view of a second embodiment of the present invention in use.
Figure 11:
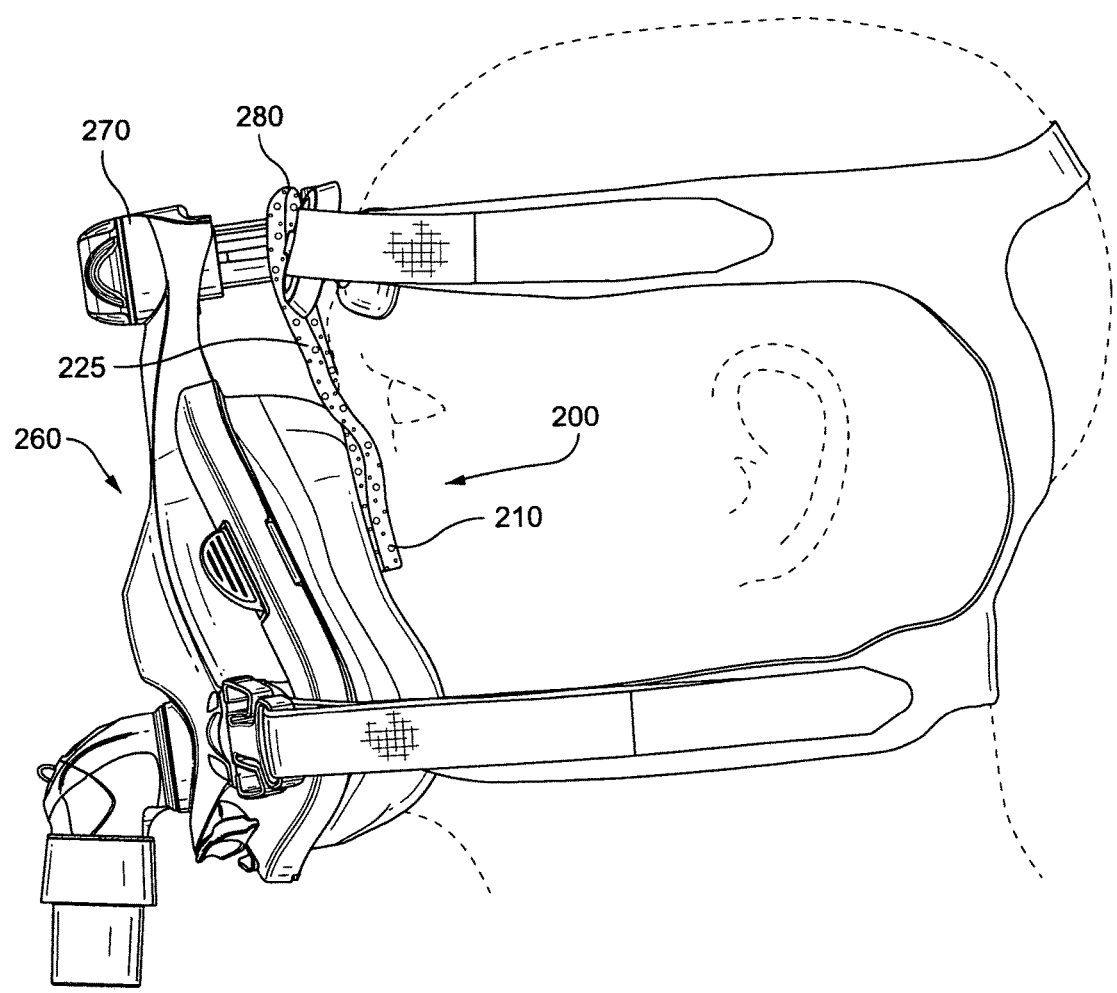
FIG. 11 shows a side view of a second embodiment of the present invention in use.
Figure 12:
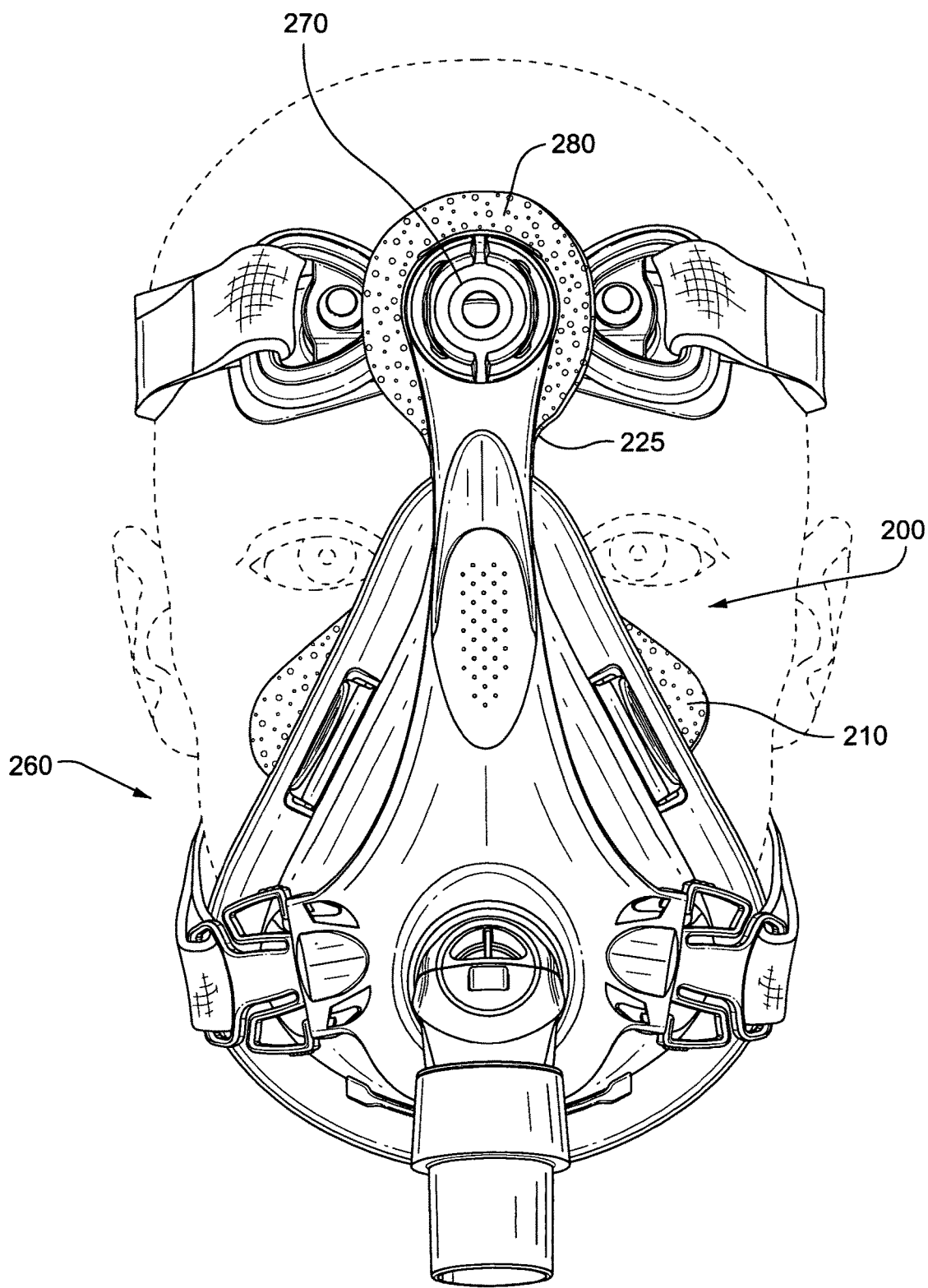
FIG. 12 shows a front view of a second embodiment of the present invention in use.
Figure 13:
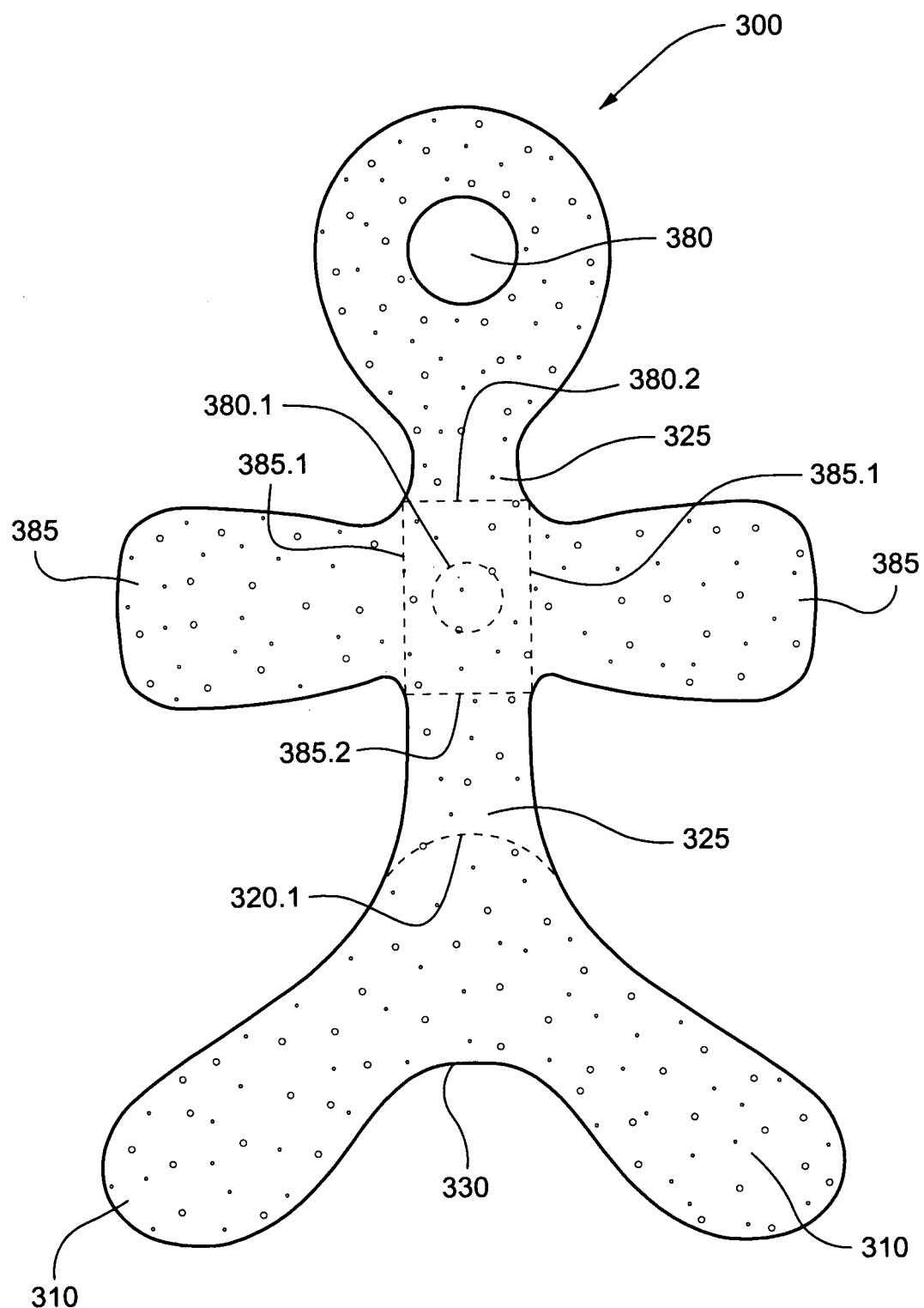
FIG. 13 shows a plan view of a third embodiment of the present invention.
Figure 14:
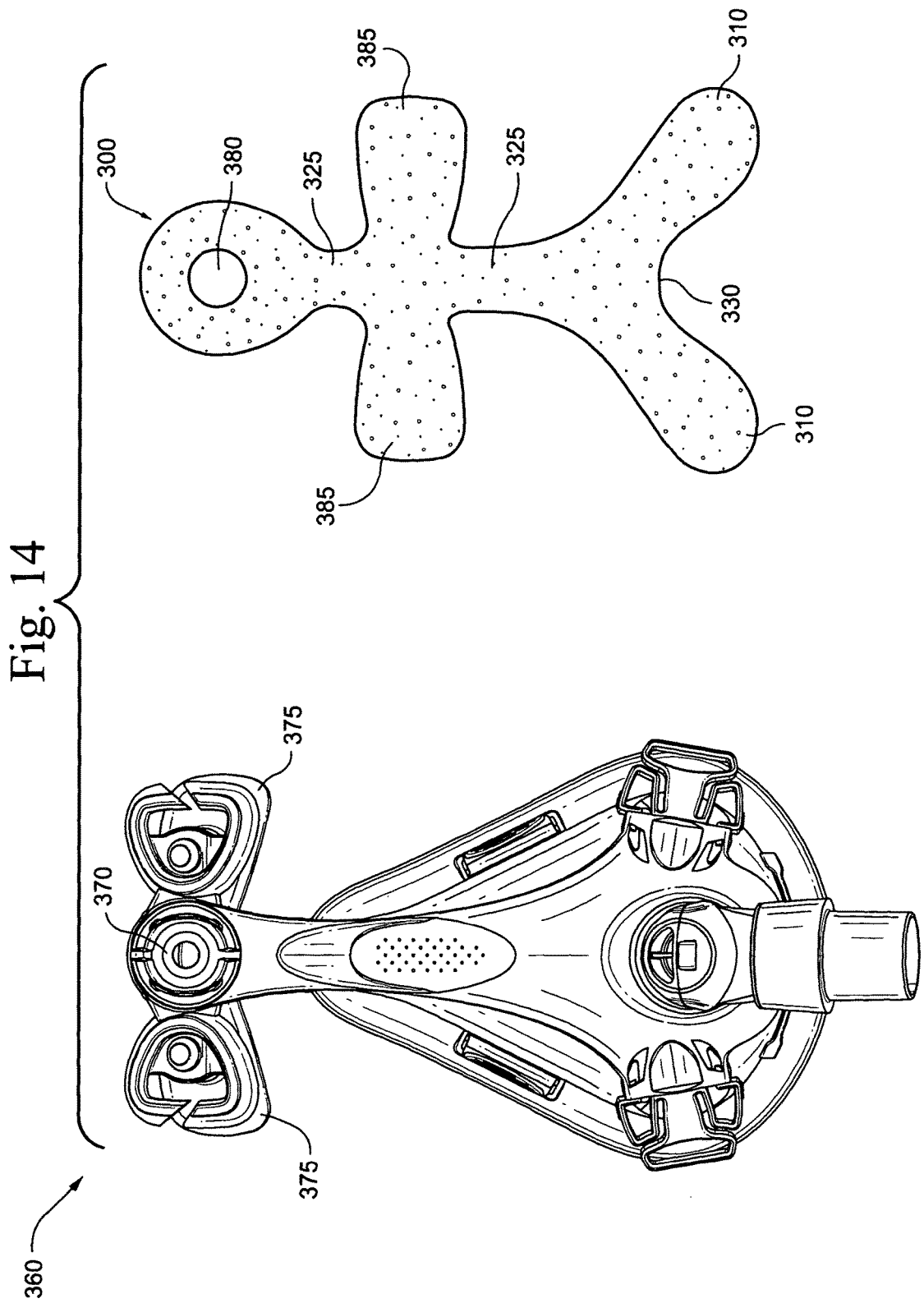
FIG. 14 shows a front view of a third embodiment of the present invention with a mask system.
Figure 15:
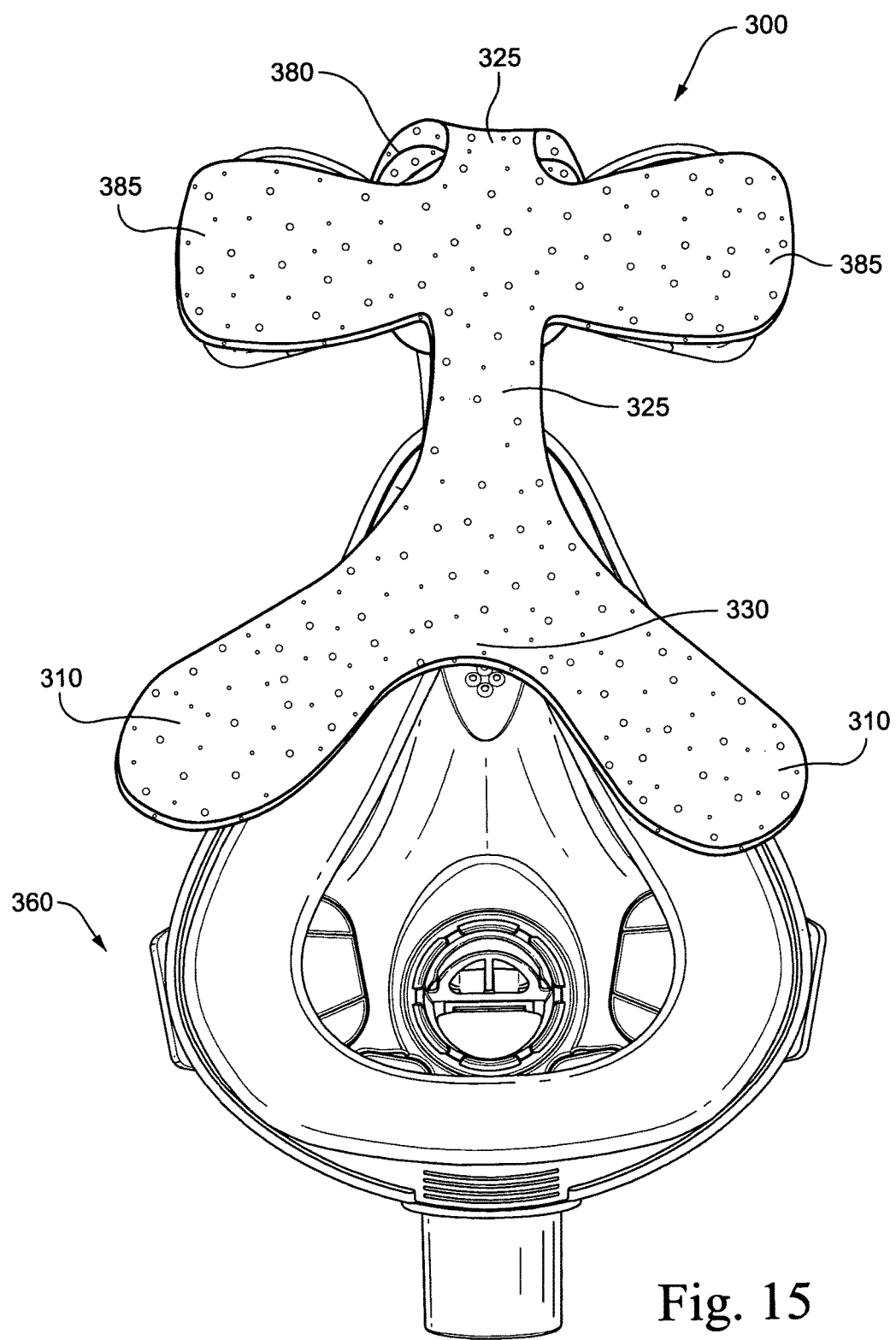
FIG. 15 shows a back view of a third embodiment of the present invention in use.
Figure 16:
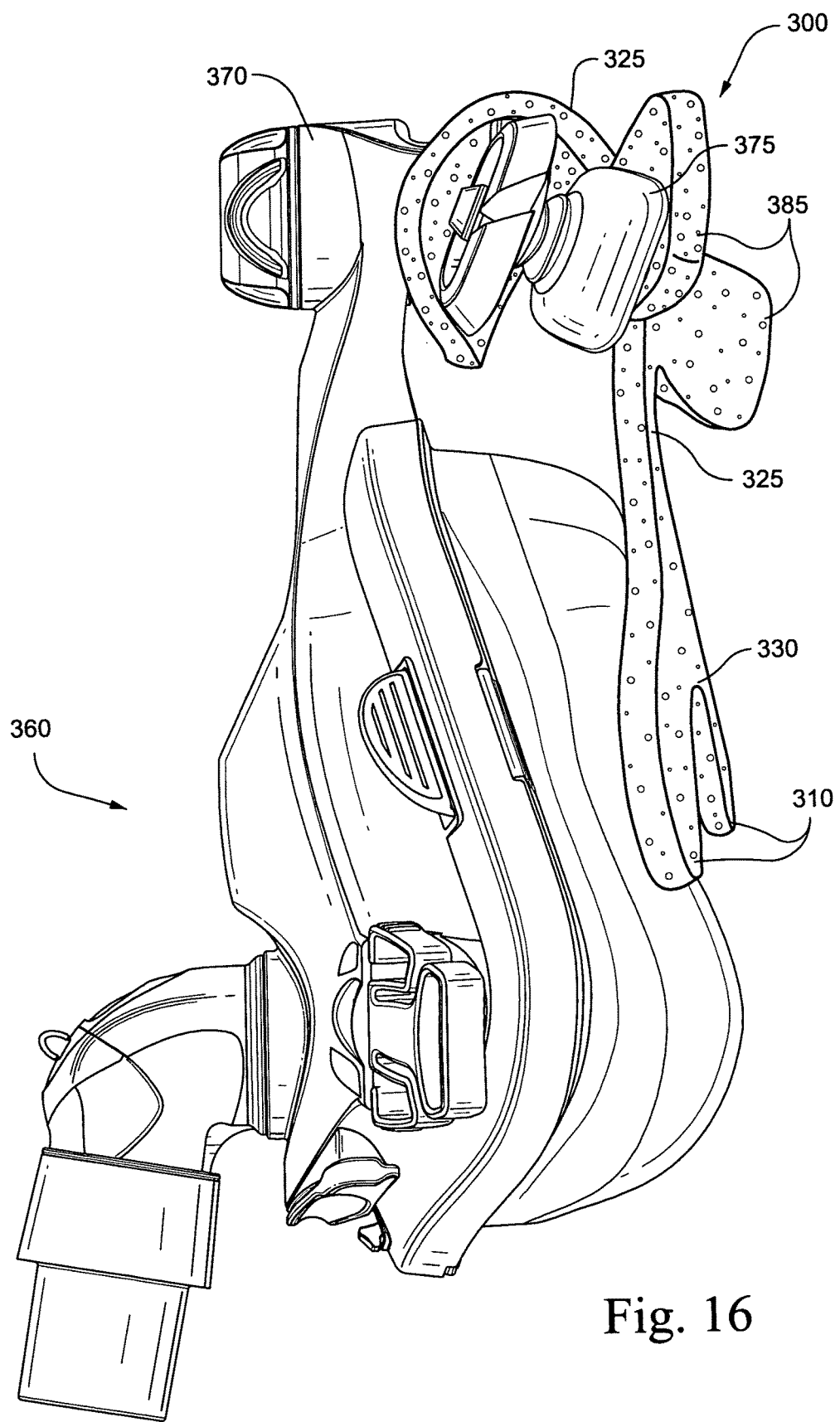
FIG. 16 shows a side view of a third embodiment of the present invention in use.
Figure 17:
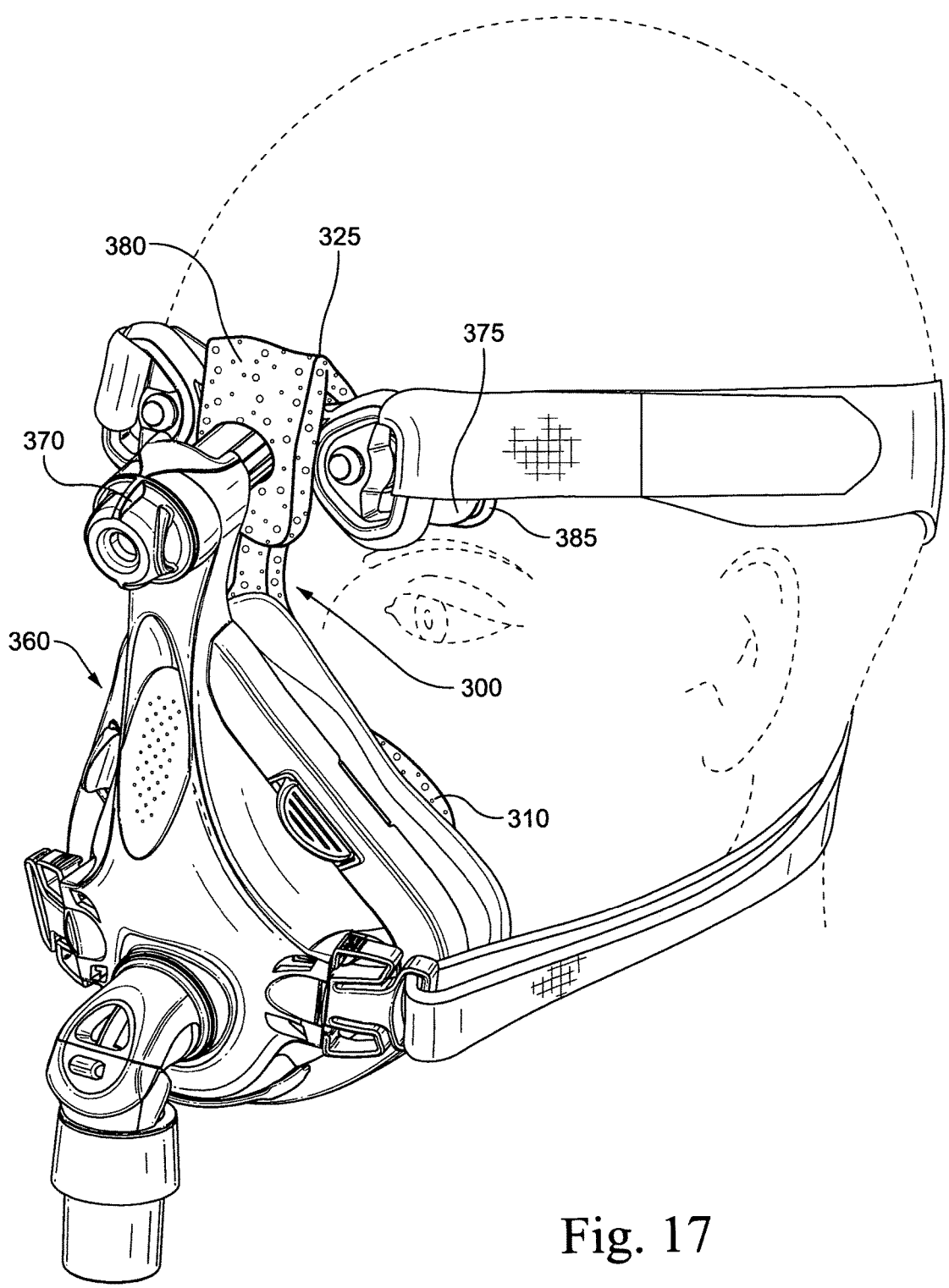
FIG. 17 shows a perspective view of a third embodiment of the present invention in use.
Figure 18:
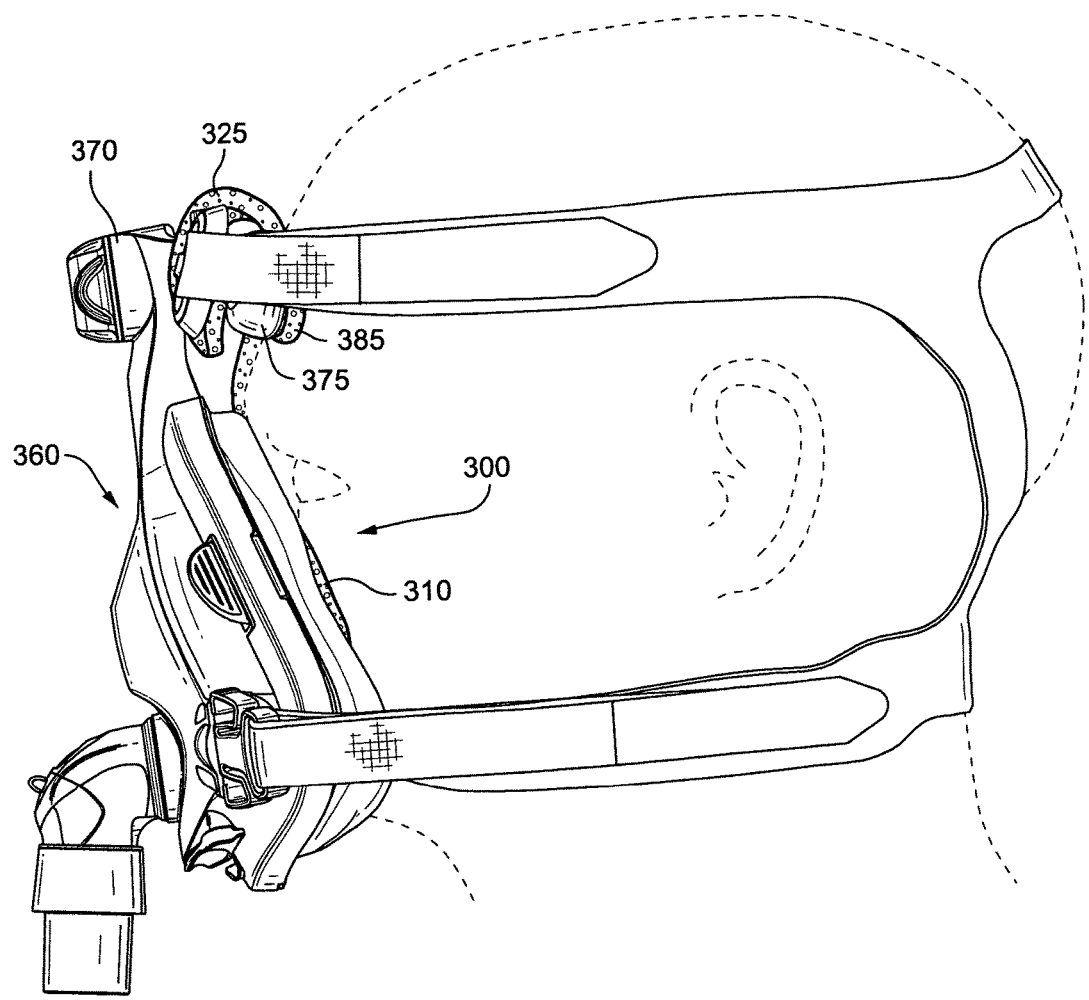
FIG. 18 shows a side view of a third embodiment of the present invention in use.
Figure 19:
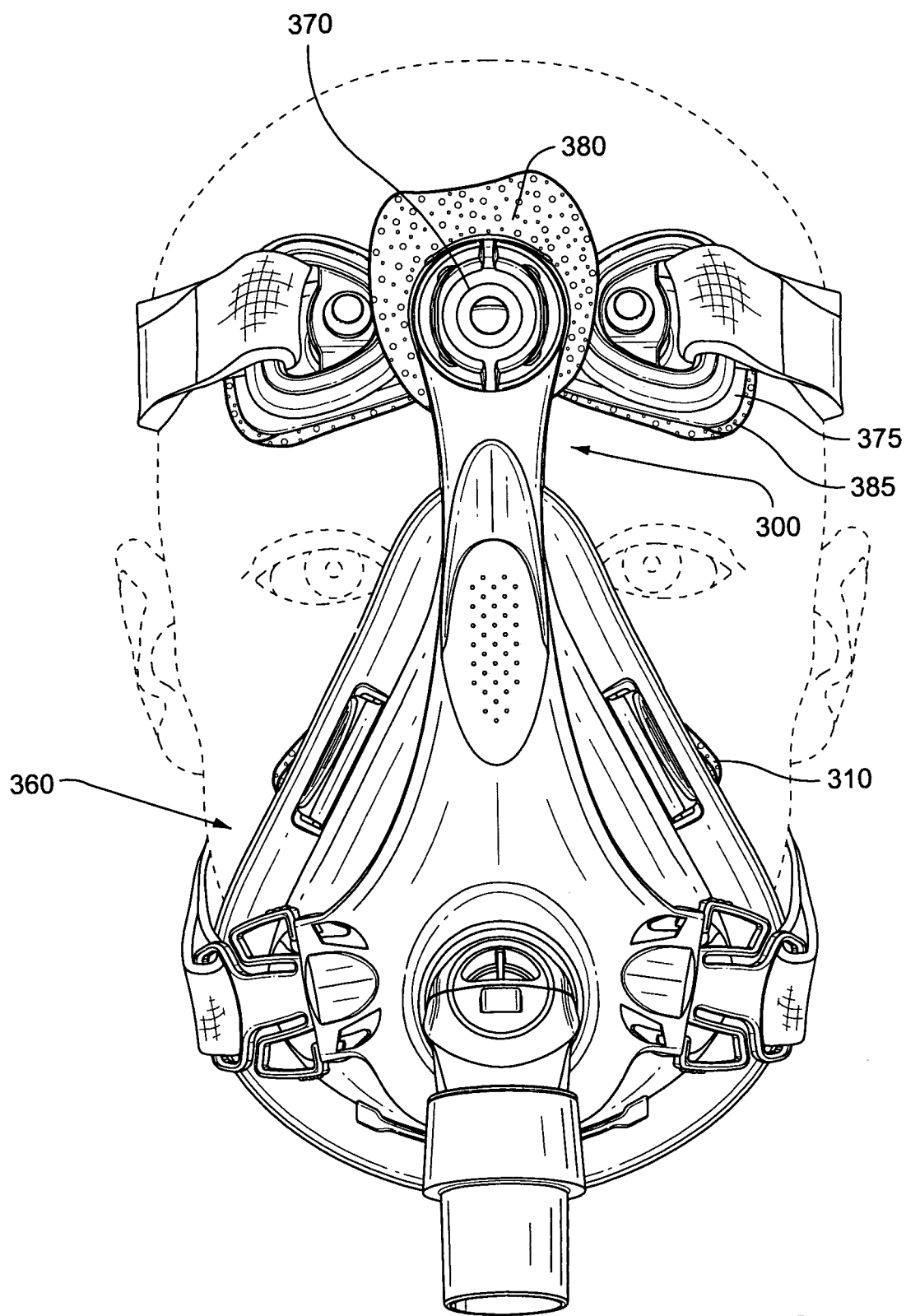
FIG. 19 shows a front view of a third embodiment of the present invention in use.

Adhesive 150 may contact the patient's face thereby applying the pad directly to the patient's skin (as shown in FIG. 3). The width of the adhesive may be about 10 mm. The mask system 160 may then be positioned on the patient's face and on top of some or all of pad 100 (as shown in FIGS. 4 and 5).

Adhesive 150 may contact the mask system 160 directly and then be applied to the patient's face (no adhesive applied to the face). Also, adhesive may be applied to both sides of the pad, to adhere to the mask system and the patient.

Pad 100 may be constructed from a flexible material. Preferably pad 100 may be constructed from a foam such as that disclosed in pending US patent application US 2008/0047560, filed 27 Jul. 2007; pending US patent application US 2008/0060649, filed 27 Jul. 2007; pending US patent application U.S. Ser. No. 12/448,250, filed 15 Jun. 2009, each incorporated herein by reference in its entirety. Other foams are also possible. Pad 100 may be constructed from fabric (e.g. woven or non-woven), gel, thermoplastic elastomer (TPE) or any other suitable material. Pad 100 may be constructed from a combination of materials e.g. fabric and foam.

Adhesive 150 may be a skin compatible adhesive such as a silicone adhesive. Adhesive may be same as those disclose in pending US patent application U.S. Ser. No. 12/478,537, filed 4 Jun. 2009, included herein by reference in its entirety. The adhesive may be a low tack adhesive.

Adhesive 150 may be covered with a release liner when not in use. Release line may be kraft paper, silicone backed paper or any other suitable material.

Preferably, pad 100 may be formed by die cutting. Pad 100 may be formed by compression cutting. Pad 100 may be formed by molding. Adhesive 150 may be laminated on to the foam before or after cutting the pad.

Pad 100 may be used with a full face mask (i.e. covering the nose and mouth of the patient), or with a nasal-only mask (i.e. cover the nose only), or with nasal pillows (prongs inserted into the patient's nose)

Advantages of the pad are that it may be disposable, intuitive to fit due to the shape and size, comfortable, enable a better or enhanced seal of the mask system when in use, and/or may encourage patient's to be compliant with therapy. The pad is ideally suited to allow both comfort and sealing in areas that are particularly sensitive, while avoiding application of extensive headgear strap tension to compensate for leaks, in which case unwanted pressure can be applied to other areas of the face, such as the cheeks and elsewhere. The pad may provide an improved seal especially with patients that have unusual facial shapes, beards/moustaches, and can assist with stability if the patient uses moisturizer or otherwise has greasy skin. The pad can also help avoid or dissipate uncomfortable leak around the patient's eyes.

Pad with Ring Attachment

In a second embodiment of the present invention, pad 200 may be provided to a mask system 260. Pad 200 may be provided with an attachment portion, e.g., a ring 280 that defines a hole 281 to attach to a portion of mask system 260, such as a forehead support 270.

As shown in FIGS. 6 to 12, pad 200 may be attached to forehead support 270 of mask system 260 by ring 280 of pad 200. Ring 280 may loop over a portion of forehead support 270 (for example, a dial portion or a joining portion 270.1 for a forehead support) such that pad 200 is positioned over the nasal bridge region of mask system 260.

Pad 200 may include a connecting region 225 to join ring 280 to distal ends 210.

Trough 230 may be provided to pad 200 to avoid the pad extending past the end of the patient's nose in use. Trough 230 may have radius of about 20 mm to 40 mm. Preferably, trough 230 may have a radius of about 30 mm.

Pad 200 may be about 100 mm to 130 mm long. Preferably, pad 200 may have a length of about 115 mm.

Pad 200 may be about 75 mm to 130 mm wide. Preferably, pad 200 may have a width of about 100 mm.

Ring 280 may have an inner diameter of about 14 mm to 18 mm. Ring 280 may have an outer diameter of about 40 mm to 44 mm.

Figure 21:
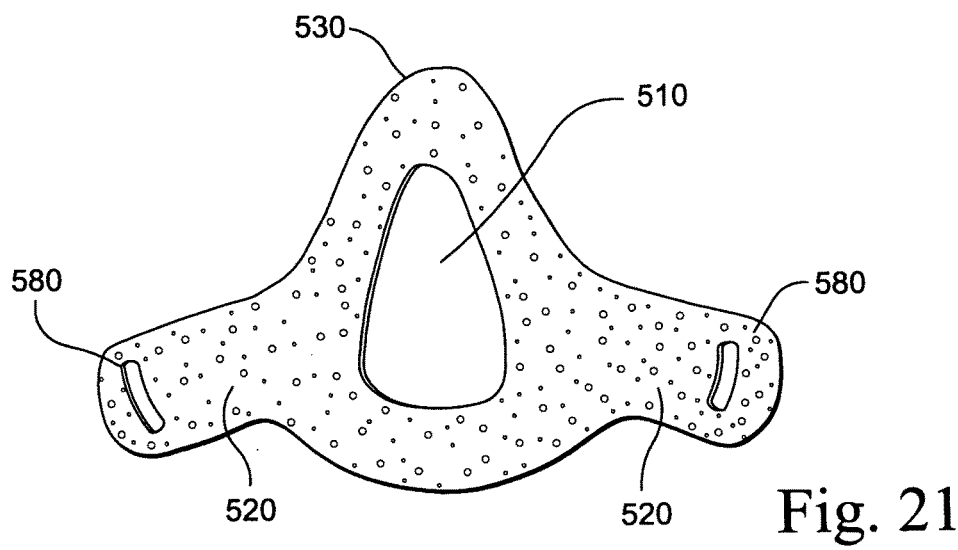
FIG. 21 shows a plan view of a fifth embodiment of the present invention.
Figure 22:
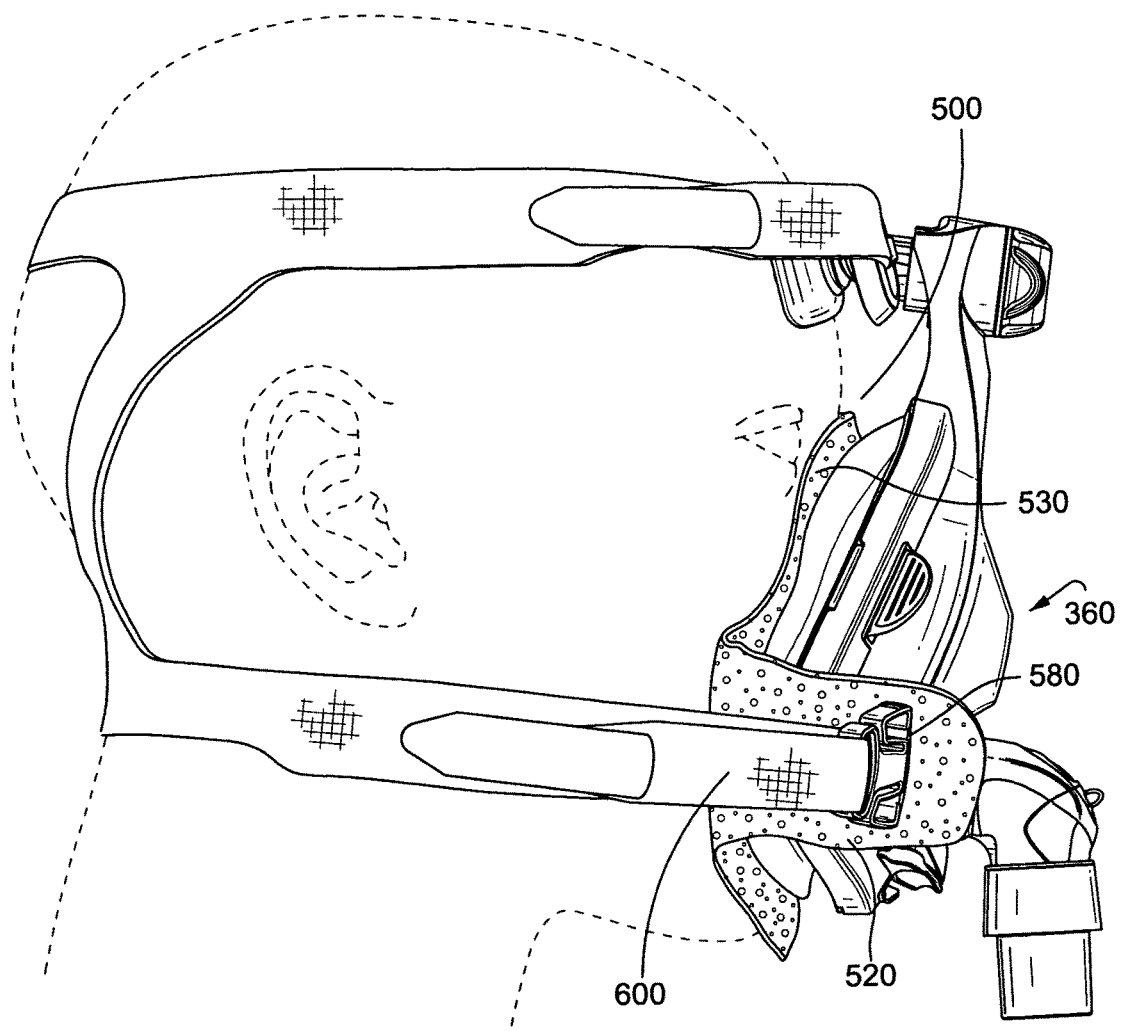
FIG. 22 shows a side view of a fifth embodiment of the present invention in use.
Figure 23:
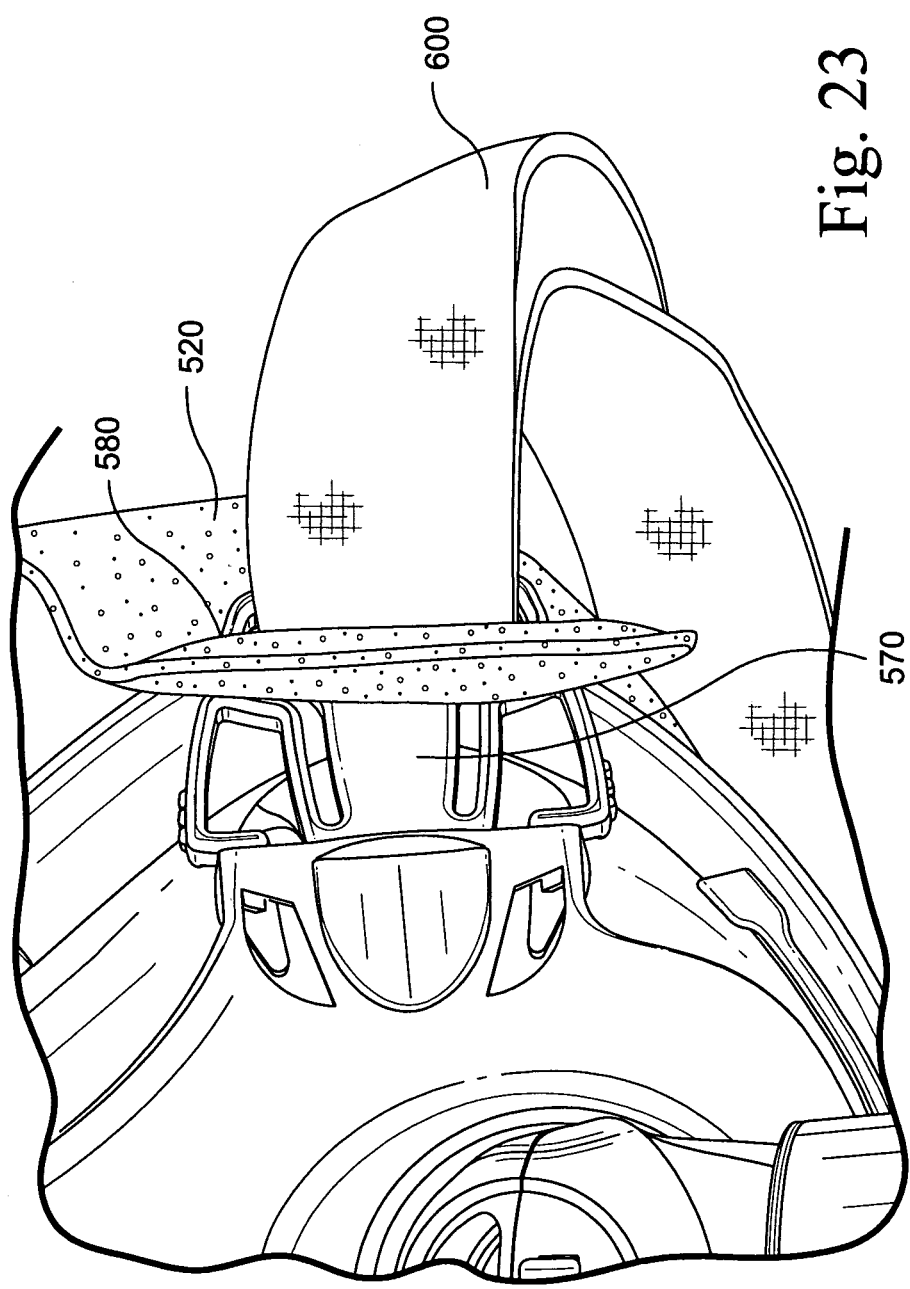
FIG. 23 shows a front view of a fifth embodiment of the present invention in use.

In an alternative form shown in FIGS. 21 to 23, pad 500 may connect or otherwise attach to headgear clips 570 or headgear 600. Pad 500 may have a main body 530 that may be shaped to match the sealing profile of mask 360, for example generally triangular, elliptical, trapezoidal. In the case of a nasal-only mask, main body includes a generally horizontal portion to extend above the upper lip. In the case of an oro-nasal mask, the horizontal portion extends below the lower lip (or on the chin). Pad 500 may include one or more attachment portions, e.g., wings or extensions 520 adapted to wrap or extend from the sealing portion of mask 360 to the headgear clips 570 or headgear 600.

Pad 500 may include an aperture 510 to receive a patient's nose and/or mouth for communication with an interior of a mask system. Pad 500, e.g., wings/extensions, may further include rings 580, e.g., in the form of an elongated aperture or slit adapted to connect or receive a headgear clip 570 or headgear 600.

In a third embodiment of the present invention, pad 300 may be provided to a mask system 360. Pad 300 may be provided with an attachment portion, e.g., a ring 380 to attach to a portion of mask system 360, such as a forehead support 370 and provide additional coverage of forehead support pads 375.

As shown in FIGS. 13 to 19, pad 300 may be attached to forehead support 370 of mask system 360 by ring 380 of pad 300. Ring 380 may loop over a portion of forehead support 370 (for example a dial portion) and may additionally fold over the top of forehead support 370, such that pad 300 is positioned over the nasal bridge region of mask system 360.

Distal ends 310 may cover some or a portion of the patient's nasal bridge region and cheeks.

At least one forehead support pad cover 385 may cover some or all of forehead support pad(s) 375 of a forehead support 370.

Pad 300 may include a connecting regions 325 to join ring 380 to forehead pad covers 385 and distal ends 310.

If desired support pad covers 385 may be attached to support pads, without the portion that contacts the nasal bridge region. The pad can have perforations, cutting lines, or pre-scored lines to render various parts removable. For example, the lateral sides of pad covers 385 can be removed along vertical score lines 385.1 to leave only that part of the pad that contacts the patient's nasal bridge region as well as the attachment portion. In another example, a horizontal perforation or score line 385.2 can be used to separate the pad covers 385 and its associated attachment portion from the main body that covers the nasal bridge region. Thus, a single pad can be produced that can be modified by the patient depending on patient preference and/or mask type, e.g., nasal-only mask in which case pad covers 385 would not be needed, or forehead pad cover and attachment portion only, or nasal bridge region with or without attachment portion. See FIG. 13. If only the nasal bridge region is to include padding, the pad is torn along contoured score line 320.1. If the nasal bridge pad is to be used with an attachment portion, then pad covers 385 are removed along score lines 385.1 in which case the upper attachment portion remains. If the upper attachment portion is inappropriately sized, another aperture (lower attachment portion) can be formed by punching out padding along score line 380.1, in which case the upper attachment portion can be separated via score lines 380.2.

Trough 330 may be provided to pad 300 to avoid the pad extending past the end of the patient's nose in use. Trough 330 may have radius of about 20 mm to 40 mm. Preferably, trough 330 may have a radius of about 30 mm.

Pad 300 may be about 155 mm to 205 mm long. Preferably, pad 300 may have a length of about 180 mm.

Pad 300 may be about 75 mm to 130 mm wide. Pad 300 may be about 95 mm to 110 mm wide. Preferably, pad 300 may have a width of about 100 mm.

Pad 300 may be about 1 mm to 15 mm thick. Preferably, pad 300 may have a thickness of about 5 mm. Preferably, pad 300 may have a thickness of about 4 mm.

Forehead support pad covers may be about 25 mm to 40 mm wide.

Ring 380 may have an inner diameter of about 14 mm to 18 mm. Ring 280 may have an outer diameter of about 40 mm to 44 mm. Ring may have a circular opening, or another shape. It may also have a slit to facilitate assembly and disassembly to/from the frame.

Pad 300 may be constructed from a flexible, breathable material. Preferably pad 100 may be constructed from a foam such as that disclosed in pending US patent application US 2008/0047560, filed 27 Jul. 2007; pending US patent application US 2008/0060649, filed 27 Jul. 2007; pending US patent application U.S. Ser. No. 12/448,250, filed 15 Jun. 2009. Other foams are also possible. Pad 300 may be constructed from fabric (e.g. woven or non-woven), gel, thermoplastic elastomer (TPE) or any other suitable material. Pad 300 may be constructed from a combination of materials e.g. fabric and foam.

Pad 300 may be used with a full face mask (i.e. covering the nose and mouth of the patient), or with a nasal-only mask (i.e. cover the nose only).

Advantages of the pad are that it may be disposable, intuitive to fit due to the shape and size, comfortable, enable a better or enhance seal of the mask system when in use, and/or may encourage patient's to be compliant with therapy.

Figure 20:
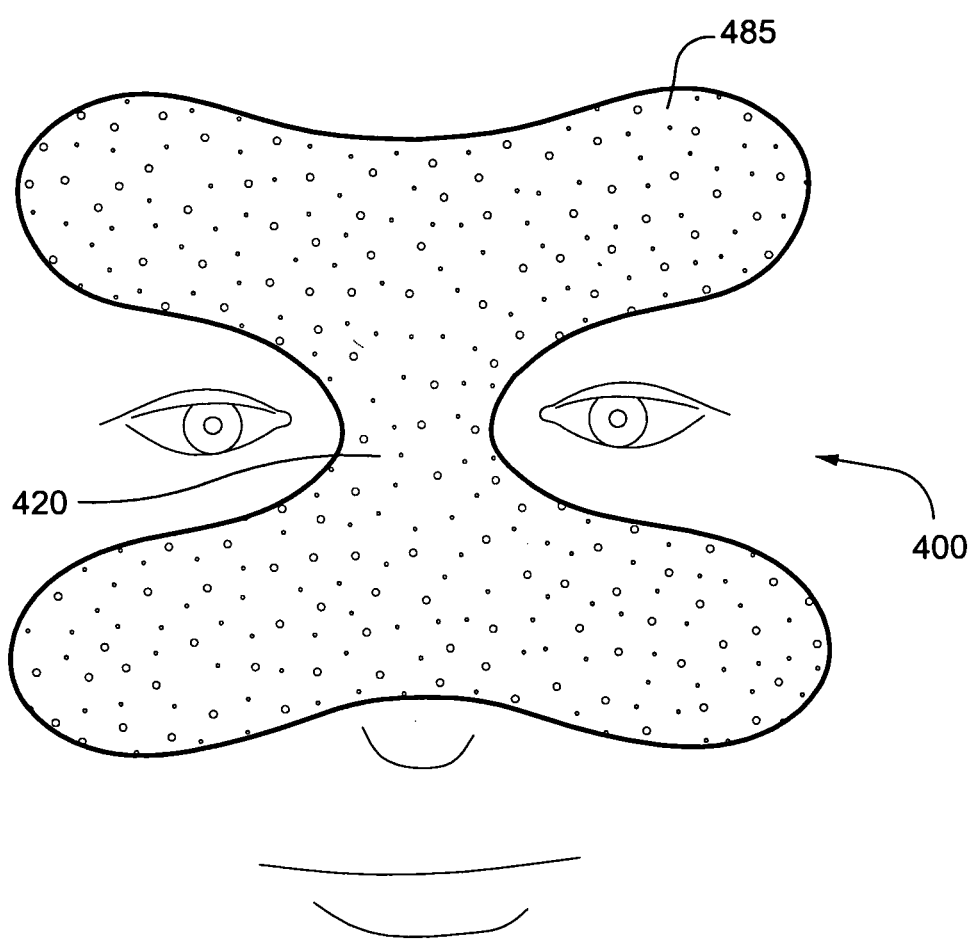
FIG. 20 shows a front view of a fourth embodiment of the present invention.

An alternative cushion pad 400 is shown in FIG. 20. Main body portion is similar to that shown in FIGS. 1 and 2. However, extending from peak portion 420 is a forehead support pad cover 485. Connecting portion 425 connects the main body and the pad cover 485. Cushion pad 400 may have a symmetrical shape so it cannot be attached (e.g., adhesively) in the wrong orientation.

Pad 100, 200, 300, 400, 500 (hereafter 'pad') may be about 1 mm to 15 mm thick. Preferably, pad may have a thickness of about 5 mm. Preferably, pad may have a thickness of about 4 mm.

Pad may be constructed from a flexible and/or conformable material. Preferably, pad may be constructed from a foam such as that disclosed in pending US patent application US 2008/0047560, filed 27 Jul. 2007; pending US patent application US 2008/0060649, filed 27 Jul. 2007; pending US patent application U.S. Ser. No. 12/448,250, filed 15 Jun. 2009. Other foams are also possible. Pad may be constructed from fabric (e.g. woven or non-woven), gel, thermoplastic elastomer (TPE) or any other suitable material. Pad may be constructed from a combination of materials e.g. fabric and foam.

Pad may be thermoformed and/or die (or compression) cut. Pad may be formed by thermoforming and ultrasonic die cutting. Alternatively, pad may be molded, for example by injection molding, compression molding, etc. In a further alternative, pad may be machined and/or stitched. Pad may be formed by any other suitable means.

Pad may be used with a full face mask (i.e. covering the nose and mouth of the patient), or with a nasal-only mask (i.e. cover the nose only).

Advantages of the pad are that it may be disposable, intuitive to fit due to the shape and size, comfortable, enable a better or enhance seal of the mask system when in use, and/or may encourage patient's to be compliant with therapy. Another advantage of a pad in accordance with the attachment and or tether aspects of the present technology is that it does not fall off the mask and get lost, or become soiled when the mask is removed from the face.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A respiratory mask system for delivery of respiratory therapy to a patient, the respiratory mask system comprising:

a mask having a frame and a cushion, the frame including a forehead support, a forehead support pad attached to the forehead support, and a joining portion that connects the forehead support to the frame; and a cushion pad comprising:
  at least one forehead support pad cover shaped and dimensioned to cover at least a portion of the forehead support pad;
  an attachment portion comprising a ring, said ring structured to receive the forehead support or the joining portion to directly attach the cushion pad to the forehead support or to the joining portion such that the cushion pad and the mask can be applied to and removed from the patient's face as a unit, the attachment portion extending from the at least one forehead support pad cover; and
  a main body portion having a central portion shaped to cover a portion of the patient's nose extending from above the nose tip to the nasal bridge region without obstructing the patient's line of sight, and the main body portion having two lateral side portions extending downward from the central portion and terminating along the sides of the nose or on the patient's cheeks at distal ends in use,
wherein the cushion pad comprises a breathable material, and
wherein a first side of the main body portion is configured to contact skin of the patient, a second side, opposite the first side, is configured to contact the cushion provided to the mask.

2. The respiratory mask system according to claim 1, wherein the breathable material comprises foam.

3. The respiratory mask system according to claim 1, wherein the cushion pad is longer than it is wide.

4. The respiratory mask system according to claim 1, wherein the cushion pad is elliptical, rectangular or trilobular in shape.

5. The respiratory mask system according to claim 1, wherein the central portion includes a peak and is adapted to cover a part of the nasal bridge region that tends to suffer the most discomfort or damage.

6. The respiratory mask system according to claim 5, wherein the peak is shaped so as to avoid obstructing the patient's line of sight.

7. The respiratory mask system according to claim 5, wherein the cushion pad has a trough so as to avoid the cushion pad extending past the tip of the patient's nose when in use.

8. The respiratory mask system according to claim 7, wherein the trough has a radius of about 20 mm to 40 mm.

9. The respiratory mask system according to claim 8, wherein the trough and the peak are complementarily shaped such that adjacent cushion pads can be easily nested when manufactured.

10. The respiratory mask system according to claim 1, wherein the cushion pad has a width of about 5 mm to 60 mm.

11. The respiratory mask system according to claim 1, wherein the cushion pad has a width of about 75 mm to 130 mm.

12. The respiratory mask system according to claim 1, wherein the cushion pad has a length of about 10 mm to 200 mm.

13. The respiratory mask system according to claim 1, wherein the cushion pad has a length of about 155 mm to 205 mm.

14. The respiratory mask system according to claim 1, wherein the cushion pad has a thickness of about 1 mm to 15 mm.

15. The respiratory mask system according to claim 14, wherein the thickness of the cushion pad is constant along a length of the cushion pad.

16. The respiratory mask system according to claim 14, wherein the thickness of the cushion pad is variable along its length and/or height.

17. The respiratory mask system according to claim 1, wherein a size of the cushion pad is adjustable.

18. The respiratory mask system according to claim 1, wherein the cushion pad includes an adhesive.

19. The respiratory mask system according to claim 18, wherein the adhesive is provided at the distal ends.

20. The respiratory mask system according to claim 18, wherein the adhesive is provided on the first side and positioned to contact the patient's skin.

21. The respiratory mask system according to claim 18, wherein the adhesive is provided on the second side to contact the mask directly.

22. The respiratory mask system according to claim 18, further comprising a release liner to cover the adhesive prior to use.

23. The respiratory mask system according to claim 1, wherein the cushion pad is constructed from a flexible material.

24. The respiratory mask system according to claim 1, wherein the cushion pad comprises foam, fabric, gel, and/or thermoplastic elastomer.

25. The respiratory mask system according to claim 1, wherein the ring is substantially round in shape.

26. The respiratory mask system according to claim 25, wherein the ring has an inner diameter of about 14-18 mm, and an outer diameter of about 40-44 mm.

27. The respiratory mask system according to claim 1, further comprising a connecting portion to connect the attachment portion to the central portion.

28. The respiratory mask system according to claim 27, wherein the connecting portion, the attachment portion, the at least one forehead support pad cover, and the main body portion are formed in one piece.

29. The respiratory mask system according to claim 1, wherein the at least one forehead support pad cover has a width of about 25 mm to 40 mm.

30. The respiratory mask system according to claim 1, wherein the at least one forehead support pad cover includes connecting regions to join the attachment portion and the central portion.

31. The respiratory mask system claim 1, wherein the cushion has a first portion structured to form a seal with the patient's skin and a second portion structured to seal with the cushion pad in use.

32. The respiratory mask system according to claim 1, wherein the at least one forehead support pad cover extends from the main body portion.

33. A respiratory mask system for delivery of respiratory therapy to a patient, the respiratory mask system comprising:
  a mask including a frame and a cushion;
  a cushion pad comprising:
    a main body portion including a central portion shaped to cover the nasal bridge region of the patient and the main body portion having two lateral side portions extending downward from the central portion and terminating along the sides of the nose or on the patient's cheeks at distal ends; and an attachment portion extending from the main body portion and the attachment portion comprising a ring defining a hole, said hole structured to receive the frame to directly attach the cushion pad to the frame,
wherein the attachment portion and the main body portion comprise one piece, and
wherein a first side of the main body portion is configured to contact skin of the patient, a second side, opposite the first side, is configured to contact the cushion.

34. The respiratory mask system according to claim 33, wherein the ring is substantially round in shape.

35. The respiratory mask system according to claim 34, wherein the ring has an inner diameter of about 14-18 mm, and an outer diameter of about 40-44 mm.

36. The respiratory mask system according to claim 33, further comprising a connecting portion to connect the attachment portion to the central portion.

37. The respiratory mask system claim 33, wherein the cushion has a first portion structured to form a seal with the patient's skin and a second portion structured to seal with the cushion pad in use.

38. The respiratory mask system according to claim 33, further comprising at least one forehead support pad cover structured to cover at least a portion of a forehead support pad of a forehead support of the mask.

39. The respiratory mask system according to claim 38, wherein the at least one forehead support pad cover has a width of about 25 mm to 40 mm.

40. The respiratory mask system according to claim 38, wherein the at least one forehead support pad cover includes connecting regions to join the attachment portion and the central portion.

41. The respiratory mask system according to claim 38, wherein the at least one forehead support pad cover extends from the main body portion.

42. The respiratory mask system according to claim 38, wherein the at least one forehead support pad cover is joined to the attachment portion.

* * * * *